United States Patent
Jiang et al.

(10) Patent No.: US 8,273,852 B2
(45) Date of Patent: Sep. 25, 2012

(54) MEDIUM CHAIN LENGTH POLYHYDROXYALKANOATE POLYMER AND METHOD OF MAKING SAME

(75) Inventors: Xuan Jiang, Dartmouth (CA); Zhiyong Sun, Dartmouth (CA); Juliana Ramsay, Harrowsmith (CA); Bruce A. Ramsay, Harrowsmith (CA)

(73) Assignee: Queen's University at Kingston, Kingston, Ontario (CA)

( * ) Notice: Subject to any disclaimer, the term of this patent is extended or adjusted under 35 U.S.C. 154(b) by 20 days.

(21) Appl. No.: 12/960,156

(22) Filed: Dec. 3, 2010

(65) Prior Publication Data

US 2011/0166318 A1    Jul. 7, 2011

Related U.S. Application Data

(60) Provisional application No. 61/267,381, filed on Dec. 7, 2009.

(51) Int. Cl.
C08G 63/02    (2006.01)
C08G 64/00    (2006.01)

(52) U.S. Cl. ....................... 528/361; 435/135
(58) Field of Classification Search ................. 435/135; 528/361
See application file for complete search history.

(56) References Cited

U.S. PATENT DOCUMENTS

| | | | |
|---|---|---|---|
| 5,296,362 | A | 3/1994 | Anderson et al. |
| 5,344,769 | A | 9/1994 | Witholt et al. |
| 6,225,438 | B1 | 5/2001 | Green |
| 7,169,598 | B2 | 1/2007 | Honma et al. |
| 2011/0020886 | A1 | 1/2011 | Yoon et al. |

FOREIGN PATENT DOCUMENTS

KR    2008/0111784    12/2008

OTHER PUBLICATIONS

Ouyang, S.-P. et al., "Production of polyhydroxyalkanoates with high 3-hydroxydodecanoate monomer content by fadB and fadA knock-out mutant of Pseudomonas putida KT2442," Biomacromolecules, vol. 8, 2504-2511 (2007).

Diard, S., et at., "Accumulation of poly(3-hydroxybutyrate) from octanoate in different Pseudomonas belonging to the the rRNA homology group I", Systematic and Applied Microbiology, vol. 25, 183-188 (2002).

Park, S.J. et al., "Enrichment of specific monomer in medium-chain-length poly(3-hydroxyalkanoates) by amplification of fadD and fadE genes in recombinant *Escherichia coli*,"Enzyme and Microbial Technology, vol. 33, 62-70 (2003).

International Search Report for International PCT Application No. PCT/CA2010/001930 filed on Dec. 3, 2010.

Written Opinion for International PCT Application No. PCT/CA2010/001930 filed on Dec. 3, 2010.

Sun, Z., Ramsay, J., Guay, M. and Ramsay B. Enhanced yield of medium-chain-length polyhydroxalkanoates from nonanoic acid by co-feeding glucose in a carbon-limited, fed-batch culture. J. Biotechnol. 143:262-267, 2009.

Sun, Z., Ramsay, J., Guay, M. and Ramsay B. Fed-batch production of unsaturated medium-chain-length polyhydroxalkanoates with controlled composition by Pseudomonas putida KT2440. Appl. Microbiol. Biotechnol. 82:657-662, 2009.

Maclean, H., Sun, Z., Ramsay, J. and Ramsay B. Decaying exponential feeding of nonanoic acid for the production of medium-chain-length poly(3-hydroxyalkanoates) by Pseudomonas putida KT2440. Can. J. Chem. 86:564-569, 2008.

Sun, Z., Ramsay, J., Guay, M. and Ramsay B. Increasing the yield of MCL-PHA from nonanoic acid by co-feeding glucose during the PHA accumulation stage in two-stage fed-batch fermentations of Pseudomonas putida KT2440. J. Biotechnol. 132:280-282, 2007.

Sun, Z., Ramsay, J., Guay, M. and Ramsay B. Carbon-limited fed-batch production of medium-chain-length polyhydroxalkanoates from nonanoic acid by Pseudomonas putida KT2440. Appl. Microbiol. Biotechnol. 74:69-77, 2007.

Choi, M.H., Hx, J., Rho, J.K., Shim, J.H. and Yoon, S.C. Shifting of the distribution of aromatic monomer-units in polyhydroxyalkanoic acid to longer units by salicylic acid in Pseudomonas fluorescens BM07 grown with mixtures of fructose and 11-phenoxyundecanoic acid. Biotechnol. Bioeng., 102: 1209-1221, 2009.

Green PR, Kemper J, Schechtman L, Guo L, Satkowski M, Fielder S, Steinbüchel A., Rehm BHA. Formation of short chain length/medium chain length polyhydroxalkanoate copolymers by fatty acid beta-oxidation inhibited Ralstonia eutropha. Biomacromolecules 3: 208-213, 2002.

Lee H-J, Rho JK, Noghabi KA, Lee SE, Choi MH, Yoon SC. Channeling of intermediates derived from medium-chain fatty acids and de novo-synthesized fatty acids to polyhydroxyalkanoic acid by 2-bromooctanoic acid in Pseudomonas fluorescens BM07. J Microbiol Biotechnol 14: 1256-1266, 2004.

Thijsse GJE. Fatty-acid accumulaltion by acrylate inhibition of beta-oxidation in alkane-oxidizing Pseudomonas. Biochim Biophys Acta 84: 195-197, 1964.

Wang H-H, Li X-T, Chen G-Q. Production and characterization of homopolymer polyhydroxyheptanoate (P3HHp) by a fadBA knock-out mutant Pseudomonas putida KTOY06 derived from P. putida KT2442. Process Biochemistry 44: 106-11, 2009.

*Primary Examiner* — Terressa Boykin
(74) *Attorney, Agent, or Firm* — Angela Lyon; Emma Saffman; Carol Miernicki Steeg

(57) ABSTRACT

A method is provided for producing medium chain length poly(3-hydroxyalkanoate) (MCL-PHA) with a selected ratio of monomers. A method of controlling the ratio of monomers in MCL-PHA is also provided which includes fermenting naturally occurring microorganisms with a fatty acid substrate, a food source and an additive. The methods provided do not sacrifice cell growth and maintenance and provide high yields of MCL-PHAs. MCL-PHAs are provided that are copolymers of $C_n$ and $C_{n-2}$ monomers, where (n is 6-18).

38 Claims, 10 Drawing Sheets

MEDIUM CHAIN LENGTH POLYHYDROXYALKANOATE POLYMER AND METHOD OF MAKING SAME

RELATED APPLICATION

This application claims the benefit of the filing date of U.S. Provisional Patent Application No. 61/267,381 filed on Dec. 7, 2009, the contents of which is incorporated herein by reference in its entirety.

FIELD OF THE INVENTION

The field of the invention is biodegradable plastic. More specifically, the field of the invention is a method of using microorganisms to prepare biodegradable polymeric materials such as medium-chain-length poly(3-hydroxyalkanoate).

BACKGROUND OF THE INVENTION

Biodegradable plastics are plastics that decompose in the natural environment. That is, upon exposure to microorganisms in the natural environment (e.g., soil), biodegradable plastics are metabolized and their molecular structure is broken down. Biodegradability in plastics is desirable because such plastics may be diverted from landfill sites. When disposed in microbially rich environments such as active compost and activated sludge, biodegradable plastics rapidly convert to nitrogen-, phosphorus-, and carbon-containing components that can be taken up by organisms such as plants. In contrast to non-biodegradable plastics, which are mostly produced from non-renewable resources such as petroleum and hydrocarbon raw materials, most biodegradable plastics are produced from renewable natural sources and provide sustainable technology. Markets for biodegradable plastics include, for example, products that end up in sewage systems and marine environments.

A particular type of biodegradable plastic is a family of polyesters called "polyhydroxyalkanoate" or simply "PHA". Besides the advantages in biodegradability, biocompatibility, and renewability compared to petrochemical plastics, PHAs also offer unique advantages such as resistance to water hydrolysis and low gas permeability when compared to other types of biodegradable plastics such as polylactides and starch-derived plastics.

Polyhydroxyalkanoates (PHAs) are polyesters synthesized and accumulated by many microorganisms. They are considered a major class of biopolymers and have attracted extensive research and industry interests in recently years. Their properties resemble those of many petroleum-based plastics, while offering inherent biodegradability and biocompatibility. However, unlike most plastics, PHAs are produced from renewable resources such as sugars and plant oils.

In the PHA polymer family there are two main types of polymers, short-chain-length poly(3-hydroxyalkanoate) (SCL-PHA) and medium-chain-length poly(3-hydroxyalkanoate) (MCL-PHA). SCL-PHAs are classified as having 3 to 5 carbons in their repeating units. MCL-PHAs are classified as having more than 5 carbons in the repeating units. Characteristics such as crystallinity and melting points differ between SCL-PHAs and MCL-PHAs. Accordingly, SCL-PHAs are better suited for certain applications while for others, MCL-PHAs are better suited.

There are numerous microorganisms that are able to synthesize SCL-PHAs such as poly(3-hydroxybutyrate) (PHB) and poly(3-hydroxybutyrate-co-3-hydroxyvalerate) (PHBV). *Cupriavidus necator*, formerly known as *Ralstonia eutropha*, is the most studied SCL-PHA-producing bacterium. SCL-PHA production by SCL-PHA-synthesizing bacteria has been well studied and it has been determined that nitrogen (N) or phosphate (P) limitation often stimulates rapid SCL-PHA synthesis. Thus, most SCL-PHA production processes employ a stage of rapid cell growth followed by a SCL-PHA accumulation stage, which is almost always N-limited or P-limited. Possibly due to an assumption that physiology of MCL-PHA-accumulating bacteria is similar to that of most SCL-PHA-accumulating bacteria, almost all publications dealing with MCL-PHA production have incorporated N or P limitation. While for certain bacterial strains, MCL-PHA production rates are stimulated by N-limitation, other strains have no improvement with N- or P-limitation (see Sun, Z. et al. (2007) *Appl. Microbiol. Biotechnol.* 74: 69-77).

As for naturally occurring MCL-PHA-producing microorganisms, MCL-PHAs have only been found in pseudomonads belonging to the rRNA homology group I, such as *Pseudomonas fluorescens* and *Pseudomonas putida* (Diard, S., et al. (2002) Syst. Appl. Microbiol. 25: 183-188).

In contrast to SCL-PHAs, MCL-PHAs are generally thermo-elastomeric materials with low melting temperature and low degree of crystallinity. Their use as biodegradable adhesives, rubbers, coatings, tissue engineering scaffolds, controlled drug delivery carriers, and toner agents has been proposed. However, due to the lack of an efficient production method for a variety of MCL-PHAs, these polyesters are not yet well studied. In particular, since under previously known technology there is no method to reliably produce MCL-PHAs with certain selected ratios of monomers, there is a lack of research as to the applications of such polymers. Thus there are unexplored avenues of new polymers. Indeed, since changing the monomeric composition of MCL-PHAs is expected to result in changes to properties of the material, there are also unexplored new uses of such new polymers. Therefore, there is a need for a method of controlling production of monomeric composition of MCL-PHA.

SUMMARY OF THE INVENTION

A first aspect of the invention provides a method of controlling microbial synthesis of MCL-PHA copolymer, comprising providing MCL-PHA-producing microbial cells in a medium suitable for microbial growth, the medium comprising a substrate that is structurally related to MCL-PHA; a carbon source that is not structurally related to MCL-PHA; and a β-oxidation pathway inhibitor; and allowing microbial cell growth to occur in the medium wherein the microbial cells produce MCL-PHA copolymer; wherein the MCL-PHA copolymer has a selected ratio of comonomers that differs from the ratio of comonomers obtained in the absence of the β-oxidation pathway inhibitor.

In an embodiment of the first aspect of the invention provides a method of controlling microbial synthesis of MCL-PHA copolymer, comprising providing MCL-PHA-producing microbial cells in a medium suitable for microbial growth, the medium comprising a substrate that is structurally related to MCL-PHA; a carbon source that is not structurally related to MCL-PHA; and a β-oxidation pathway inhibitor; allowing microbial cell growth to occur in the medium wherein the microbial cells produce MCL-PHA copolymer; collecting the MCL-PHA copolymer; wherein the MCL-PHA copolymer has a selected ratio of comonomers that differs from the ratio of comonomers obtained in the absence of the β-oxidation pathway inhibitor.

In other embodiments of the first aspect, the structurally-related substrate is a fatty acid. In certain embodiments of the first aspect, the structurally-related substrate is a $C_6$-$C_{18}$ fatty acid. In some embodiments of the first aspect, the structurally-related substrate is hexanoic acid, heptanoic acid, octanoic acid, nonanoic acid, decanoic acid, undecanoic acid, or dodecanoic acid.

In some embodiments of the first aspect, the carbon source is not susceptible to β-oxidation. In some embodiments of the first aspect, the MCL-PHA-producing microbial cells are of the genus *Pseudomonas*.

In an embodiment of the first aspect, the structurally-related substrate is a functionalized fatty acid. In certain embodiments of the first aspect, the functionalized fatty acid is a functionalized hexanoic acid, functionalized heptanoic acid, functionalized octanoic acid, functionalized nonanoic acid, functionalized decanoic acid, functionalized undecanoic acid, or functionalized dodecanoic acid.

In an embodiment of the first aspect, the β-oxidation pathway inhibitor is acrylic acid, 2-butynoic acid, 2-octynoic acid, phenylpropionic acid, propionic acid, trans-cinnamic acid, salicylic acid, methacrylic acid, 4-pentenoic acid, or 3-mercaptopropionic acid.

In an embodiment of the first aspect, the carbon source is a carbohydrate, glycerol, citric acid, acetic acid, lactic acid, or a combination thereof. In certain embodiments of the first aspect, the method further comprises purifying the collected MCL-PHA. In certain embodiments of the first aspect, the carbon source is added in a fed-batch manner or a continuous manner.

A second aspect of the invention provides a method of making MCL-PHA polymer, comprising: providing MCL-PHA-producing microbial cells in a medium suitable for microbial growth, the medium comprising: a substrate that is structurally related to MCL-PHA; a carbon source that is not structurally related to MCL-PHA; and a β-oxidation pathway inhibitor; and allowing microbial cell growth to occur in the medium wherein the microbial cells synthesize MCL-PHA polymer; wherein the MCL-PHA polymer is a homopolymer or a copolymer that has a selected ratio of comonomers that differs from that obtained in the absence of the β-oxidation pathway inhibitor.

Another embodiment of the second aspect provides a method of making MCL-PHA polymer, comprising providing MCL-PHA-producing microbial cells in a medium suitable for microbial growth, the medium comprising a substrate that is structurally related to MCL-PHA; a carbon source that is not structurally related to MCL-PHA; and a β-oxidation pathway inhibitor; allowing microbial cell growth to occur in the medium wherein the microbial cells synthesize MCL-PHA polymer; and collecting the MCL-PHA polymer, wherein the MCL-PHA polymer is a homopolymer or a copolymer that has a selected ratio of comonomers that differs from that obtained in the absence of the β-oxidation pathway inhibitor.

Embodiments of the second aspect provide a method of making MCL-PHA polymer, wherein MCL-PHA-producing microbial cells are genetically modified microorganisms. In certain embodiments, the genetic modification increases production of PHA, increases oxygen uptake capacity, increases solvent toxicity resistance, decreases autolysis, modifies the ratio of PHA comonomers, or any combination thereof. In some such embodiments modifying the ratio of PHA comonomers is increasing the amount of predominant monomer. In other embodiments of the second aspect the MCL-PHA-producing microbial cells are naturally occurring.

In certain embodiments of the second aspect, the structurally-related substrate is a fatty acid. In some embodiments of the second aspect, the structurally-related substrate is a $C_6$-$C_{18}$ fatty acid. In certain embodiments of the second aspect, the structurally-related substrate is nonanoic acid or octanoic acid. In certain embodiments of the second aspect, the carbon source is not susceptible to β-oxidation. In some embodiments of the second aspect, the MCL-PHA-producing microbial cells are of the genus *Pseudomonas*.

In some embodiments of the second aspect, the structurally-related substrate is a functionalized fatty acid. In some embodiments of the second aspect, the functionalized fatty acid is a functionalized hexanoic acid, functionalized heptanoic acid, functionalized octanoic acid, a functionalized nonanoic acid, a functionalized decanoic acid, a functionalized undecanoic acid, or a functionalized dodecanoic acid. In some embodiments of the second aspect, the β-oxidation pathway inhibitor is acrylic acid, 2-butynoic acid, 2-octynoic acid, phenylpropionic acid, propionic acid, trans-cinnamic acid, salicylic acid, methacrylic acid, 4-pentenoic acid, or 3-mercaptopropionic acid. In certain embodiments of the second aspect, the carbon source is a carbohydrate such as glucose or sucrose. In certain embodiments of the second aspect, the method further comprises purifying the collected MCL-PHA. In certain embodiments of the second aspect, the carbon source is added in a fed-batch manner or a continuous manner.

A third aspect of the invention provides a polyhydroxyalkanoate polymer produced by the method of the second aspect, that is at least about 89 mol % or higher of a selected monomer. In certain embodiments of the third aspect, the at least about 89 mol % or higher is 89 mol %. In certain embodiments of the third aspect, the at least about 89 mol % or higher is 90 mol %. In certain embodiments of the third aspect, the at least about 89 mol % or higher is 95 mol %. In certain embodiments of the third aspect, the at least about 89 mol % or higher is 99 mol %. In some embodiments of the third aspect, the structurally-related substrate is hexanoic acid, heptanoic acid, octanoic acid, nonanoic acid; decanoic acid, undecanoic acid, or dodecanoic acid. In some embodiments of the third aspect, the β-oxidation pathway inhibitor is acrylic acid, 2-butynoic acid, 2-octynoic acid, phenylpropionic acid, propionic acid, trans-cinnamic acid, salicylic acid, methacrylic acid, 4-pentenoic acid, or 3-mercaptopropionic acid.

A fourth aspect of the invention provides poly(3-OH-nonanoate-co-3-OH-heptanoate) (PHN) comprising about 71 mol % or higher 3-OH-nonanoate. In embodiments of the fourth aspect, the PHN comprises about 75, about 81, about 83, about 86, about 88, about 90, about 92, about 94, about 95, or about 96 mol % 3-OH-nonanoate.

A fifth aspect of the invention provides poly(3-OH-octanoate-co-3-OH-hexanoate) (PHO) comprising about 89 mol % or higher 3-OH-octanoate. In embodiments of the fifth aspect, the PHO comprises about 93, about 94, about 96, about 97, or about 98 mol % 3-OH-octanoate.

A sixth aspect of the invention provides polyhydroxyalkanoate polymer comprising a $C_n$ monomer that has n carbons and a $C_{n-2}$ monomer that has n−2 carbons, where n is 8 to 12, and where the polymer is at least 70 mol % $C_n$ monomer.

A seventh aspect of the invention provides polyhydroxyalkanoate polymer comprising a $C_n$ monomer that has n carbons, where n is 6 to 18, and where the polymer is 70 mol % or higher $C_n$ monomer.

An eighth aspect of the invention provides polyhydroxyalkanoate polymer comprising a $C_n$ monomer that has n carbons, where n is 6 to 12, and where the polymer is 70 mol % or higher $C_n$ monomer.

A ninth aspect of the invention provides polyhydroxyalkanoate polymer comprising a $C_n$ monomer that has n carbons, where n is 8 to 18, and where the polymer is 70 mol % or higher $C_n$ monomer.

In embodiments of the sixth to ninth aspects, the $C_n$ monomers is: 3-OH-hexanoate, 3-OH-heptanoate, 3-OH-octanoate, 3-OH-nonanoate, 3-OH-decanoate, 3-OH-undecanoate, or 3-OH-dodecanoate. In some embodiments of the sixth and seventh aspects, the at least 70 mol % is 80 mol %. In some embodiments, the at least 70 mol % is 85 mol %. In some embodiments, the at least 70 mol % is 90 mol %. In some embodiments, the at least 70 mol % is 95 mol %. In some embodiments, the at least 70 mol % is 99 mol %.

In some embodiments of the sixth to ninth aspects, the 70 mol % or higher is 100 mol %.

Another aspect of the invention provides a polyhydroxyalkanoate polymer produced by the method of the first aspect, that is at least about 89 mol % or higher of a selected monomer. In some embodiments, the at least about 89 mol % is 89 mol %. In some embodiments, the at least about 89 mol % is 90 mol %. In some embodiments, the at least about 89 mol % is 95 mol %. In some embodiments, the at least about 89 mol % is 99 mol %. In some embodiments, the at least about 89 mol % is 100 mol %.

Embodiments of this aspect provide a polyhydroxyalkanoate polymer, wherein the structurally-related substrate is octanoic acid, nonanoic acid; decanoic acid, undecanoic acid, or dodecanoic acid.

Yet another embodiment of this aspect provides polyhydroxyalkanoate polymer, wherein the β-oxidation pathway inhibitor is acrylic acid, 2-butynoic acid, 2-octynoic acid, phenylpropionic acid, propionic acid, trans-cinnamic acid, salicylic acid, methacrylic acid, 4-pentenoic acid, or 3-mercaptopropionic acid.

Another aspect of the invention provides a polyhydroxyalkanoate polymer comprising a $C_n$ monomer that has n carbons and a $C_{n-2}$ monomer that has n−2 carbons, where n is 6 to 18, and where the polymer is at least about 89 mol % or higher $C_n$ monomer.

Yet another aspect of the invention provides a polyhydroxyalkanoate polymer comprising a Cn monomer that has n carbons, where n is 6 to 18, and where the polymer is 89 mol % or higher Cn monomer.

An aspect of the invention provides a polyhydroxyalkanoate polymer comprising a $C_n$ monomer that has n carbons, wherein when n is 6, 7, 9, 10, or 11, the polymer is at least about 71 mol % or higher $C_n$ monomer, wherein when n is 8, the polymer is at least about 89 mol % or higher $C_n$, monomer, and wherein when n is 12 to 18, the polymer is at least about 21 mol % or higher $C_n$ monomer.

Yet another aspect of the invention provides a polyhydroxyalkanoate polymer prepared in the presence of a β-oxidation pathway inhibitor, comprising a ratio of comonomers that differs from the ratio of comonomers obtained in the absence of β-oxidation pathway inhibition.

An embodiment of this aspect provides polyhydroxyalkanoate polymer, wherein the $C_n$ monomer is: 3-OH-hexanoate, 3-OH-heptanoate, 3-OH-octanoate, 3-OH-nonanoate, 3-OH-decanoate, 3-OH-undecanoate, or 3-OH-dodecanoate.

Another aspect of the invention provides a polyhydroxyalkanoate polymer comprising about 21 mol % or higher 3-OH-dodecanoate.

Another aspect of the invention provides a polyhydroxyalkanoate polymer comprising at least about 35 mol % or higher 3-OH-dodecanoate.

Yet another aspect of the invention provides a polyhydroxyalkanoate polymer comprising at least about 60 mol % or higher 3-OH-dodecanoate.

In another aspect the invention provides polyhydroxyalkanoate polymer of any of the preceeding aspects, wherein the MCL-PHA-producing microbial cells are genetically modified microorganisms. In certain embodiments, the genetic modification increases production of PHA, increases oxygen uptake capacity, increases solvent toxicity resistance, decreases autolysis, modifies the ratio of PHA comonomers, or any combination thereof. In some such embodiments modifying the ratio of PHA comonomers is increasing the amount of predominant monomer. In other embodiments of this aspect the MCL-PHA-producing microbial cells are naturally occurring.

Other objects and advantages of the present invention will become apparent from the disclosure herein.

BRIEF DESCRIPTION OF THE DRAWINGS

For a better understanding of the invention and to show more clearly how it may be carried into effect, reference will now be made by way of example to the accompanying drawings, which illustrate aspects and features according to embodiments of the present invention, and in which:

FIG. 2A is a plot of biomass concentration (see • symbols and left y-axis), PHA content (see □ symbols and right y-axis), and residual acrylic acid concentration (AA, see ▲ symbols and right secondary y-axis) versus inflow acrylic acid concentration (x-axis). FIG. 2B is a plot of monomeric composition ($C_9$ and $C_7$) of collected MCL-PHA versus inflow acrylic acid concentration.

FIG. 3A is a plot of biomass concentration (see • symbols and left y-axis), PHA content (see □ symbols and right y-axis) and residual acrylic acid concentration (AA, see ▲ symbols and right secondary y-axis) versus inflow acrylic acid concentration (x-axis). FIG. 3B is a plot of monomeric composition of isolated MCL-PHA ($C_9$ and $C_7$) versus inflow acrylic acid concentration.

FIG. 4A is a plot of biomass concentration (see • symbols and left y-axis), PHA content (see □ symbols and right y-axis)

and residual acrylic acid concentration (AA, see ▲ symbols and right secondary y-axis) versus inflow acrylic acid concentration (x-axis). FIG. 4B is a plot of monomeric composition of isolated MCL-PHA ($C_8$ and $C_6$) versus inflow acrylic acid concentration.

FIG. 10A is a plot of biomass concentration (see ● symbols and left y-axis), PHA content (see □ symbols and right y-axis) versus inflow acrylic acid concentration (x-axis). FIG. 10B is a plot of monomeric composition of isolated MCL-PHA ($C_{12}$, $C_{10}$, $C_8$ and $C_6$) versus inflow acrylic acid concentration.

DETAILED DESCRIPTION OF THE INVENTION

Definitions

Figure 1:
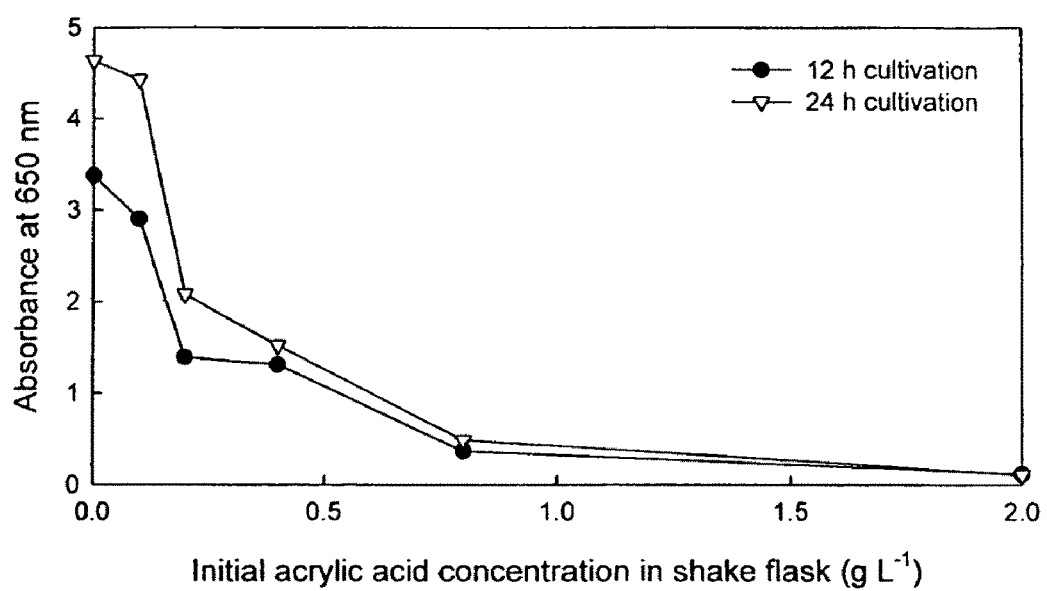
FIG. 1 is a plot of Absorbance at a wavelength (λ) of 650 nm for shake flask cultures of *Pseudomonas putida* KT2440 grown at various initial concentrations of acrylic acid; data is presented for culturing times of 12 h (•) and 24 h (∇).

The term "monomer" as used herein means a repeating unit of a polymer. The term "comonomer" as used herein means one of at least two monomers that are present in a polymer. The term "polymer" as used herein means a molecular chain of subunits that may be linear or branched, and includes homopolymers and copolymers. The term "homopolymer" as used herein means a polymer with a single repeating unit. The term "copolymer" as used herein means a polymer with at least two different repeating units.

As used herein, "aliphatic" refers to hydrocarbon moieties that are straight chain, branched or cyclic, may be alkyl, alkenyl or alkynyl, and may be substituted or unsubstituted.

The term "PHA" as used herein means polyhydroxyalkanoate.

The term "MCL-PHA" as used herein means medium-chain-length poly(3-hydroxyalkanoate) which are poly(3-hydroxyalkanoates classified as having more than 5 carbons in their repeating units.

The term "SCL-PHA" as used herein means short-chain-length poly(3-hydroxyalkanoate) which are poly(3-hydroxyalkanoates classified as having 3 to 5 carbons in their repeating units.

The term "SCL-co-MCL PHA" as used herein means a copolymer of SCL-PHA and MCL-PHA.

The term "PHO" as used herein means a PHA comprising at least 50 mole % of 3-OH-octanoic acid monomer (i.e., predominant monomer is 3-OH-octanoic acid). The term "PHN" as used herein means a PHA comprising at least 50 mole % of 3-OH-nonanoic acid monomer (i.e., predominant monomer is 3-OH-nonanoic acid). The term "PHDD" as used herein means a PHA comprising at least 50 mole % of 3-OH-dodecanoic acid monomer (i.e., predominant monomer is 3-OH-dodecanoic acid).

The term "functionalized" is intended to encompass compounds bearing a substituent(s) selected from the group consisting of halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphate ester, phosphonato, phosphinato, cyano, amino, acylamino, amide, imino, sulfhydryl, alkylthio, arylthio, thiocarboxylate, dithiocarboxylate, sulfate, sulfonato, sulfamoyl, sulfonamido, nitro, nitrile, trifluoromethyl, azido, heterocyclyl, aromatic, and heteroaromatic moieties, ether, epoxide, ester, anhydride, boron-containing moieties, silicon-containing moieties and combinations of any of these.

The term "structurally-related substrate" means a compound that can be metabolized via a β-oxidation pathway (see FIG. 9) by MCL-PHA-synthesizing-microbial cells to generate a MCL-PHA precursor. Examples of structurally-related carbon sources include: aliphatic acids such as octanoic acid, nonanoic acid, decanoic acid; or compounds that can be oxidized to form aliphatic acids such as octane, nonane, and decane.

The terms "structurally-unrelated" and "not structurally related" mean a compound that is metabolized by MCL-PHA-synthesizing-microbial cells by metabolic routes other than the β-oxidation pathway (i.e., not susceptible to β-oxidation).

The term "carbon source" refers to a nutrient (such as sugar) that provides carbon needed for cellular respiration, cellular combustion, and/or synthesis of new organic molecules.

The terms "β-oxidation inhibitor" and "β-oxidation pathway inhibitor" refer to a chemical compound that inhibits an enzyme(s) of the fatty acid β-oxidation pathway.

The term "$C_6$" is used for convenience to represent a polyhydroxyalkanoate monomer that has six carbons (three of the carbons in its backbone and three carbons in its sidechain). The term "$C_7$" is used for convenience to represent a polyhydroxyalkanoate monomer that has seven carbons (three of the carbons in its backbone and four carbons in its sidechain). The term "$C_8$" is used for convenience to represent a polyhydroxyalkanoate monomer that has eight carbons (three of the carbons in its backbone and five carbons in its sidechain). The term "$C_9$" is used for convenience to represent a polyhydroxyalkanoate monomer that has nine carbons (three of the carbons in its backbone and six carbons in its sidechain). The term "$C_{10}$" is used for convenience to represent a polyhydroxyalkanoate monomer that has ten carbons (three of the carbons in its backbone and seven carbons in its sidechain). The term "$C_{11}$" is used for convenience to represent a polyhydroxyalkanoate monomer that has eleven carbons (three of the carbons in its backbone and eight carbons in its sidechain). The term "$C_{12}$" is used for convenience to represent a polyhydroxyalkanoate monomer that has twelve carbons (three of the carbons in its backbone and nine carbons in its sidechain). See Table 1 for structural formulae of examples of polyhydroxyalkanoates discussed herein.

Description

As described above, PHA has attracted commercial interest since it is renewable, biodegradable and biocompatible. PHA has properties similar to polyethylene, polypropylene, synthetic polyesters and acrylics, but it can be produced from renewable resources. Suggested uses for currently produced PHAs include packaging such as fast food containers, disposable syringes and bottles, and coatings. MCL-PHAs are a distinct group of polymers in the PHA family that have more than five carbons in their monomer units. In particular, MCL-PHAs with 6 to 14 carbons in their repeating units show promise in latex form, and as thermoelastomers for biomedical applications such as drug delivery and tissue engineering.

Aspects of the invention provide methods of controlling the monomeric ratio of MCL-PHA produced by microbial cells; optionally, the microbial cells are wild type. Prior to this invention, it has not been possible to produce MCL-PHA with certain selected ratios of comonomers. Such monomeric ratio control is obtained by modulating a metabolic pathway that is involved both in MCL-PHA synthesis and in energy generation. By using culturing strategies that are described herein, MCL-PHAs were produced that differ significantly from MCL-PHAs that were produced by previously known methods using the same microorganism. Accordingly, the invention provides a method of making a variety of copolymers with a broad range of properties.

Aspects of the invention provide polyhydroxyalkanoates with a broad range of monomeric ratios. In contrast, previously known methods used mutant or recombinant microorganisms and provided PHAs of limited monomeric compositions. Also, the efficiency of such methods was typically low. MCL-PHAs produced by methods of the invention significantly expand the range of compositions and properties of MCL-PHAs as a class of biopolyester. Advantageously, methods of the invention to produce MCL-PHAs possess such efficiency that they are capable of being easily scaled up for industrial production.

MCL-PHAs are produced by naturally occurring microorganisms such as *Pseudomonas* species of the rRNA homology group I (Diard, S., et al. (2002) *Syst. Appl. Microbiol.* 25:183-188), for example, *Pseudonomas putidta* KT2440 (ATCC (American Type Culture Collection) No. 47054). To facilitate such production, microorganisms are fermented under appropriate conditions. Conditions to be maintained during fermentation include appropriate levels of nutrients, dissolved oxygen, temperature and pH. Required nutrients include carbon-, nitrogen-, phosphorus-, and sulfur-containing sources as well as mineral salts.

Figure 9:
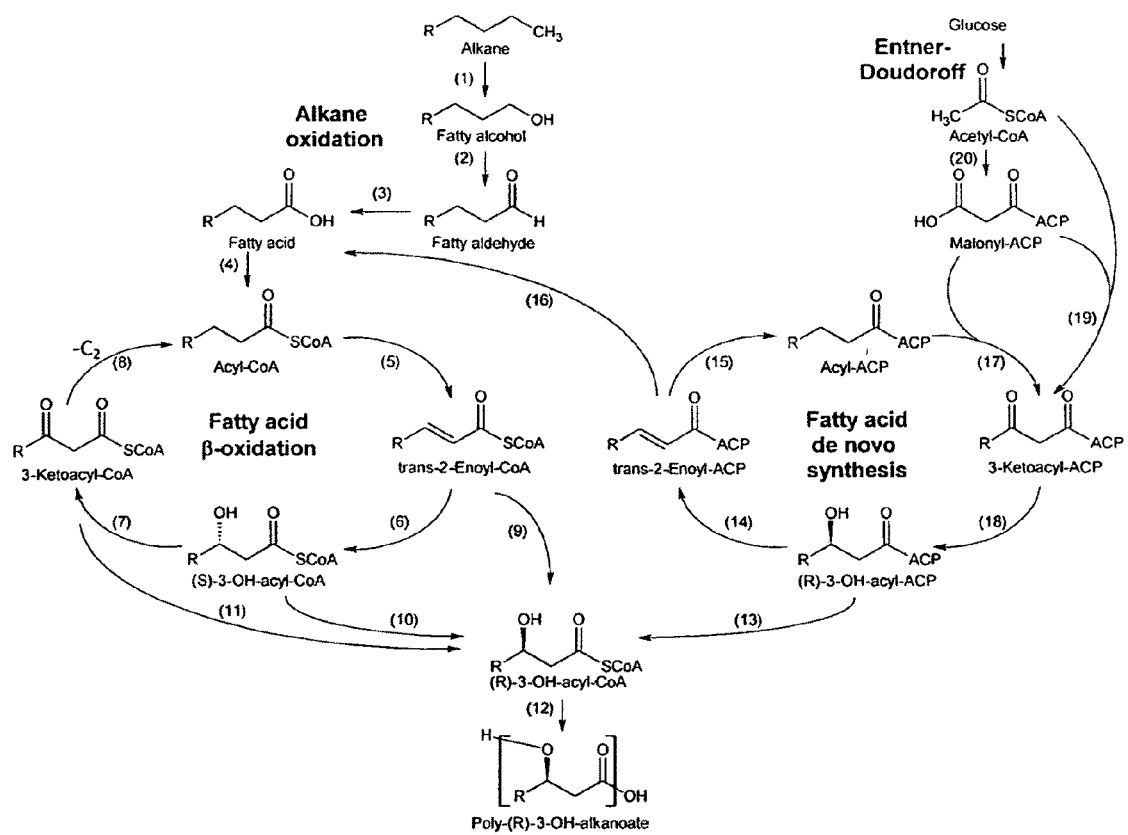
FIG. 9 is a schematic of major pathways involved in MCL-PHA synthesis by pseudomonads (Adapted from Vanderleij F R, Witholt B (1995) "Strategies for the sustainable production of new biodegradable polyesters in plants—a review." *Canadian Journal of Microbiology* 41:222-238). Confirmed or postulated enzymes of each step are numbered as follows: alkane hydroxylase (1); alcohol dehydrogenase (2); aldehyde dehydrogenase (3); thiokinase (4); acyl-CoA dehydrogenase (5); enoyl-CoA hydratase or crotonase, (6); (S)-3-OH-acyl-CoA dehydrogenase (7); 3-ketoacyl-CoA thiolase (8); enoyl-CoA hydratase (9); 3-OH-acyl-CoA epimerase (10); ketoacyl-CoA reductase (11); PHA polymerase (12); (R)-3-OH-acyl (ACP-CoA) transferase (13); 3-OH-acyl-ACP dehydratase (14); enoyl-ACP reductase (15); fatty acid thioesterase (16); 3-ketoacyl synthase (17); ketoacyl-ACP dehydratase (18); ketoacyl-ACP synthase (19); and acetyl-CoA carboxyltransferase and malonyl-CoA ACP transacylase (20).

Methods of the invention may be applied to any microorganism capable of producing MCL-PHA from structurally-related carbon sources via the fatty acid β-oxidation route of MCL-PHA synthesis (see FIG. 9). Such microorganisms include, but are not limited to, rRNA homology group I *Pseudomonas* (Diard, S., et al. (2002) *Syst. Appl. Microbiol.* 25: 183-188), for example, *Pseudomonas putida* (e.g., strains KT2440 and GPo1), *Pseudomonas aeruginosa* (e.g., strain PAO), *Pseudomonas resinovorans, Pseudomonas citronellolis* and *Pseudomonas fluorescens*. The microorganism may also be a recombinant strain if a similar β-oxidation MCL-PHA synthesis route is present, for example, recombinant *Escherichia coli*. Among the above microorganisms, *Pseudomonas putida* is most typically used. A description of microorganisms belonging to the genus *Pseudomonas* may be found in "Bergey's Manual of Systematic Bacteriology", $2^{nd}$ edition, vol. 2 (2005), part B, Gammaproteobacteria, p. 323-379, George M. Garrity (editor).

The microorganisms may be cultured in any conventional way of bacterial cultivation, such as, for example, in a batch mode shake flask, in a batch mode bioreactor fermentation, in a fed-batch mode bioreactor fermentation, and in a continuous bioreactor fermentation.

In aspects of the invention, culture medium contains (i) a structurally-related carbon source, (ii) a structurally-unrelated carbon source, (iii) a β-oxidation inhibitor, and other nutrients generally necessary for microbial growth. Such nutrients are typically added to the culture medium in water soluble salt forms, and include nitrogen, phosphorus, sulfur, magnesium, sodium, potassium, iron, and other trace metal elements. Other culture conditions such as temperature, pH, and dissolved oxygen (DO) also need to be maintained at appropriate levels for the culture.

As discussed in more detail herein, non-limiting examples of (i) structurally-related carbon sources include: fatty acids such as $C_6$-$C_{18}$ fatty acids which include nonanoic acid, octanoic acid, decanoic acid, undecanoic acid, dodecanoic acid; and functionalized $C_6$-$C_{18}$ fatty acids which include functionalized nonanoic acid, functionalized octanoic acid, functionalized decanoic acid and functionalized undecanoic acid.

As discussed in more detail herein, non-limiting examples of (ii) structurally-unrelated carbon sources include carbohydrate such as glucose or sucrose, or any other energy source that is not susceptible to β-oxidation, such as glycerol, citric acid and acetic acid.

As discussed in more detail herein, non-limiting examples of (iii) β-oxidation inhibitors include acrylic acid, 2-butynoic acid, 2-octynoic acid, phenylpropionic acid, propionic acid, trans-cinnamic acid, salicylic acid, methacrylic acid, 4-pentenoic acid, and 3-mercaptopropionic acid.

Prior to describing embodiments of the invention, the pathways of MCL-PHA production will be briefly presented to describe how microorganisms produce MCL-PHA and why there are at least two monomers present in MCL-PHAs produced by previously known methods.

As shown schematically in FIG. 9, there are two major biochemical pathways responsible for MCL-PHA synthesis: Fatty Acid β-oxidation and Fatty Acid de novo synthesis, with the former being the predominant and most efficient route of PHA synthesis. In Fatty Acid β-oxidation, a carbon source that is structurally-related to PHA is converted to PHA. This pathway is indicated on the left side of FIG. 9 starting at fatty acid. In Fatty Acid de novo synthesis, a carbon source that is structurally-unrelated to PHA is converted to PHA. This pathway is indicated on the right side of FIG. 9 starting at glucose or a similar carbohydrate compound.

As shown in FIG. 9, the β-oxidation pathway utilizes substrates that are structurally-related to PHA, such as fatty acids, aliphatic alkanes, alkenes, and intermediates thereof, in the synthesis of MCL-PHA. In Fatty Acid β-oxidation, fatty acids are oxidized sequentially into enoyl-CoA, acyl-CoA, and ketoacyl-CoA (steps 5, 6, and 7) before two carbons are removed from the ketoacyl-CoA in the form of acetyl-CoA (step 8). After such a cycle, the acyl-CoA with two carbons less than the previous acyl-CoA enters the β-oxidation cycle again. It is postulated that any of the three intermediates of one β-oxidation cycle can be transformed into (R)-3-hydroxy-acyl-CoA (steps 9, 10, 11), which is the only stereoisomeric precursor accepted by the MCL-PHA synthase, and polymerized into MCL-PHA (step 12). Due to the cyclic nature of β-oxidation, the PHA that is produced has at least two comonomers that differ from one another by one $C_2$ unit (e.g., $C_9$ and $B_7$) (Lee, S.Y., et al. (2000) *Biotechnol. Bioeng.* 68:466-470).

When nonanoic acid, for example, is the fatty acid carbon source on the left side of FIG. 9, a $C_9$ comonomer is present in the resulting MCL-PHA product by following one of three enzymatic paths: (4), (5) and (9); (4), (5), (6) and (10); or (4), (5), (6), (7) and (11). The presence of $C_7$ in the product is due to the β-oxidation pathway loop shown in FIG. 9 at enzyme step (8). During this step, one $C_2$ unit departs from the $C_9$-bearing 3-ketoacyl-CoA, leaving a $C_7$-bearing Acyl-CoA. This $C_7$-species then follows one of the enzymatic paths: (5) and (9); (5), (6) and (10); or (5), (6), (7) and (11).

When a certain combination of microbial culture and structurally-related substrate is provided, the synthesized MCL-PHA always has the same monomeric composition with little variation. For example in U.S. Pat. No. 5,344,769, *Pseudomonas oleovorans* GPo1 grown on octanoate always produced poly(3-OH-octanoate-co-3-OH-hexanoate-co-3-OH-decanoate), with 90% 3-OH-octanoate as the predominant monomer. *Pseudomonas fluorescens* grown on octanoate produced similar copolymers with 63% 3-OH-octanoate as the predominant monomer. In the inventors' own study using *Pseudomonas putida* KT2440 grown on nonanoate under substantially previously described conditions, it always produced poly(3-OH-nonanoate-co-3-OH-heptanoate) with about 70% 3-OH-nonanoate as the predominant monomer.

On the other hand, as illustrated on the right side of FIG. 9, De novo fatty acid synthesis allows the conversion of non-structurally-related carbon-containing compounds (e.g., carbohydrates such as glucose and sucrose) into MCL-PHA under culture conditions by using limitations of certain nutrients (Sanchez, R. J., Schripsema, J., da Silva, L. F., Taciro, M. K., Pradella, J. G. C., Gomez, J. G. C. (2003) *European Polymer Journal* 39:1385-1394; U.S. Pat. No. 5,296,362). This route results in a copolymer with hydroxydecanoate ($C_{10}$) and hydroxyoctanoate ($C_8$) as its major components together with other minor monomer units that also have an even-number of carbons. Again, with a given microorganism culture and carbon source, the synthesized MCL-PHA has a consistent monomeric composition. For example, *Pseudomonas* sp. NCIB 40135 grown on glucose yielded poly(3-OH-decanoate-co-3OH-octanoate) with 85% 3-OH-decanoate as the predominant monomer (U.S. Pat. No. 5,296,362). In general, such MCL-PHA synthesis route is much less efficient energetically than the direct fatty acid β-oxidation route, as considerable energy is required to produce MCL-fatty acids from structurally-unrelated carbon compounds.

As stated previously, MCL-PHAs synthesized by conventional methods have limited variation in monomeric composition and physical properties. Such MCL-PHAs have low melting temperatures and a low degree of crystallinity. In order to expand the applicability of MCL-PHA, it is important to obtain a wider variety of monomeric compositions than naturally occurs with a given combination of culture and carbon source. To this end, researchers have tried to amplify or knock out specific genes coding for certain enzymes involved in β-oxidation, in order to alter the monomeric composition of MCL-PHA. It was reported by Park et al. in *Enzyme and Microbial Technology* 33 (2003) 62-70 that, by amplifying the fadD and fadE genes in recombinant *Escherichia coli*, MCL-PHA with enriched 3-OH-decanoate molar content was obtained when sodium decanoate was used as the carbon source. It was also reported by Ouyang at al. in *Biomacromolecules* 8 (2007) 2504-2511 that, by knocking out fadB and fadA genes of certain wild type *Pseudomonas putida*, MCL-PHA with enriched monomers having the same number of carbons as the employed alkanoate substrates could be obtained. MCL-PHA with very high relative amounts of one monomer over the other, ultimately approaching a substantially homopolymeric PHA (see U.S. Pat. No. 7,169,598 by Honma et al.) was also attained. However, most of the aforementioned studies used strains that are not naturally occurring, and more importantly, none of the aforementioned studies was able to demonstrate any control over the monomeric composition of the MCL-PHAs that were attained by the engineered cultures. Given a certain combination of the engineered strain and the carbon source used, the monomeric compositions that may be achieved are still limited. Since β-oxidation is the energy generating pathway of a microorganism culture when fatty acids are used as energy source, when enzymes in this pathway are knocked out, it generally results in slower culture growth and prolonged cultivation time, which is unfavorable for industrial production of MCL-PHA.

In the discussion of so-called naturally occurring organisms above, it is understood that the inventors are referring to pathways associated with PHA production not having been genetically manipulated or otherwise mutagenized. Whether or not or mutations or recombinant molecules are present in unrelated loci of the organisms is not pertinent to the spirit of the invention. For example, the presence or absence of an antibiotic resistance gene or other common marker is not material.

Aspects of the invention provide inhibiting of the β-oxidation pathway to control the ratio of comonomers in the MCL-PHA product. Studies described herein have been conducted to determine the effects of inhibiting the β-oxidation pathway on cell growth, PHA content, and PHA monomer ratios. Such studies are described in the working examples, figures, and tables. In studies described herein, acrylic acid was used as a β-oxidation pathway inhibitor. The concentration of acrylic acid was varied to quantify its effects. Other β-oxidation pathway inhibitors are expected to have similar results. Without wishing to be bound by theory, the inventors suggest that the mechanism of action of acrylic acid as a β-oxidation inhibitor involves interaction with β-ketoacyl-CoA thiolase.

β-ketoacyl-CoA thiolase acts at conversion step (8) of FIG. 9, before chain scission of 3-ketoacyl-CoA to form Acyl-CoA with one $C_2$ unit less that the Acyl-CoA that is obtained through conversion step (4). By inhibiting the β-oxidation pathway at this site, generation of energy required for cell growth and maintenance is substantially decreased, and many accumulated intermediates are diverted to PHA synthesis. Unless efficient cell growth and maintenance are achieved in another way, inhibition of the β-oxidation pathway results in low cell concentrations and low PHA accumulation. Accordingly, when the β-oxidation pathway was inhibited, cell growth was maintained by providing a carbon-source that was structurally-unrelated to PHA. This structurally-unrelated carbon source was used for energy production and cell growth while the C-source that was structurally-related to PHA was used for PHA production. Therefore, with the combination of a structurally-related carbon source, a structurally-unrelated carbon source, and a β-oxidation inhibitor, not only was the final MCL-PHA composition successfully modulated, but good cell growth and MCL-PHA content were also attained.

As introduced briefly above, an aspect of the invention provides a method of controlling the ratio of monomers in MCL-PHA by growing bacteria in the presence of representatives from three groups of compounds. These three groups are: (i) a carbon source that is structurally-related to PHA; (ii) a carbon source that is structurally-unrelated to PHA but that supports cell growth; and (iii) a β-oxidation pathway inhibitor.

The first group, (i) a substrate that is structurally-related to PHA, comprises carbon sources that can be converted to MCL-PHA synthesis precursors substantially directly via the fatty acid β-oxidation pathway, which is shown in FIG. 9. Their structure is similar to the structure of the repeating units in the resulting MCL-PHA. Structurally-related compounds include, but are not limited to: alkanes such as heptane, octane, nonane, decane, undecane, dodecane; alkenes such as heptene, octene, nonene, decene, undecene, dodecene; alcohols such as hexanol, heptanol, octanol, nonanol, decanol; saturated and unsaturated aliphatic acids and their salt form such as hexanoic acid, heptanoic acid, octanoic acid, nonanoic acid, decanoic acid, undecanoic acid, dodecanoic acid, octanoic acid, nonenoic acid, undecenoic acid, sodium heptanoate, sodium octanoate, sodium nonanoate; and long chain fatty acids such as lauric acid, oleic acid. Preferably, medium-chain-length fatty acids or their salt forms are used, such as octanoate, nonanoate, and undecenoate. Octanoic acid may be conveniently derived from coconut and palm kernel oils. Nonanoic acid may be produced from oleic, linoleic, erucic and other carboxylic acids derived from temperate zone plants such as, for example, canola. The structurally-related carbon source may be used in an amount that is sufficient for MCL-PHA production but does not inhibit the growth of the culture. In a shake flask culture or batch fermentation culture, usually up to 20 g $L^{-1}$ can be used, preferably up to 10 g $L^{-1}$, more preferably up to 3 g $L^{-1}$. In a fed-batch fermentation culture, the feeding of the carbon source is carried out such that the concentration of the carbon source in the bioreactor does not exceed 20 g $L^{-1}$, preferably does not exceed 10 g $L^{-1}$, and more preferably does not exceed 3 g $L^{-1}$. In continuous cultivation, the carbon source concentration in the inflow medium can be relatively high, as long as the concentration in the bioreactor does not exceed the concentrations that are acceptable in cultivation.

The second group, (ii) a carbon-source that is not structurally-related to PHA but that supports cell growth, does so through Entner-Doudoroff pathway and Krebs cycle, or Embden-Meyerhof pathway (glycolysis) and Krebs cycle. Structurally-unrelated carbon sources include, but are not limited to: saccharides such as glucose, fructose, sucrose, and mannose; glycerol; organic acids such as acetic acid; and complex carbon sources such as nutrient broth, tryptone, and yeast extract. In certain embodiments of the invention the structurally-unrelated carbon source is a saccharide such as glucose. The structurally-unrelated carbon source may be used in a concentration that is sufficient for biomass and energy generation but does not inhibit the growth of the culture. In shake flask culture or batch fermentation culture, up to 40 g $L^{-1}$ of structurally-unrelated carbon source can be used. In some embodiments of the invention, up to 10 g $L^{-1}$ of structurally-unrelated carbon source is used. In certain embodiments up to 5 g $L^{-1}$ of structurally-unrelated carbon source is used. In a fed-batch fermentation culture, the feeding of the carbon source is carried out such that the concentration of the carbon source in the bioreactor does not exceed 20 g $L^{-1}$ preferably does not exceed 10 g $L^{-1}$, and more preferably does not exceed 5 g $L^{-1}$. In continuous cultivation, the structurally-related carbon source concentration in the inflow medium can be relatively high, as long as the concentration in the bioreactor does not exceed the concentrations that are acceptable in cultivation.

The third group is (iii) a β-oxidation pathway inhibitor. By inhibiting the β-oxidation pathway, the amount of group (I) substrate that completes the β-oxidation pathway is controlled. This pathway includes conversion of 3-ketoacyl-CoA to acyl-CoA through enzyme (8) 3-ketoacyl-CoA thiolase, such that the acyl-CoA is modified to have one less $C_2$ unit than (i). Examples of fatty acid β-oxidation inhibitors include, but are not limited to, acrylic acid, 2-butynoic acid, 2-octynoic acid, phenylpropionic acid, propionic acid, trans-cinnamic acid, salicylic acid, methacrylic acid, 4-pentenoic acid, and 3-mercaptopropionic acid. The inhibitors may be an acid form or a corresponding salt form, such as, for example, sodium acrylate. In certain embodiments of the invention, acrylic acid or acrylate is the preferred β-oxidation inhibitor. The inhibitor may be used in an amount that will be sufficient to modulate the β-oxidation pathway and the final MCL-PHA compositions, but at a level such that the growth of the culture is not substantially inhibited. In continuous cultivation, the inhibitor concentration in the inflow medium may be 0 to 10 mM depending on the desired final MCL-PHA composition. In a shake flask culture or batch fermentation culture, the initial inhibitor concentration may be up to 10 mM depending on the desired final MCL-PHA composition. In fed-batch fermentation culture, the feeding of the inhibitor is carried out such that the concentration of the inhibitor in the reactor does not exceed 10 mM, and preferably not exceed 4 mM, while the feeding amount depends on the desired final MCL-PHA composition.

Through embodiments of the invention, the inventors have demonstrated that it is possible to produce from microbial cells, a MCL-PHA copolymer having a selected ratio of monomers. Another aspect of the invention provides a method to produce from microbial cells, MCL-PHA having a selected specific monomer content. For both aspects, the microbial cells may be wild type, i.e., not genetically engineered. Embodiments of the invention that are described herein were tested and produced high cell concentration, high PHA content, and high yield. Monomer content was controlled by the amount of (iii) β-oxidation pathway inhibitor that was added, the choice of and the ratio of (i) and (ii).

In a particular embodiment of the invention, *Pseudomonas* species of the rRNA homology group I microorganisms were grown and fed in a manner well established in the art and detailed in the Working Examples. The growth medium comprised a compound from each of the three groups in a controlled manner, (i) nonanoic acid; (ii) glucose, and (iii) acrylic acid. By cofeeding the microorganisms with nonanoic acid and glucose, PHA production and energy generation were both possible using different metabolic pathways. The resulting MCL-PHA had the selected ratio of comonomers.

In an aspect of the invention, a method is provided such that a MCL-PHA is produced with a chosen ratio of comonomers. For both PHN MCL-PHAs and PHO MCL-PHAs, such ratios include: 100:0; 99:1; 98:2; 97:3; 96:4; 95:5; 94:6; 93:7; 92:8; 91:9; 90:10; 89:11; 88:12; 87:13; 86:14; 85:15; 84:16; 83:17; 82:18; 81:19; 80:20; 79:21; 78:22; 77:23; 76:24; 75:25; 74:26; 73:27; 72:28; 71:29; 70:30; 69:31; 68:32; 67:33; 66:34; and 65:35.

Each ratio of comonomers provides a product with distinct characteristics that is suited to particular applications. Accordingly, a method is provided such that MCL-PHAs with a variety of relative amounts of monomer (e.g., 80:20, 85:15, 90:10; 95:5) can be reliably produced.

In an embodiment of the invention, step (8) of the β-oxidation pathway (FIG. 9) is completely inhibited and none of the carbon-source proceeds through step (8), so none of the carbon-source has one two-carbon unit removed and thus, a homopolymeric MCL-PHA is produced. For example, when the carbon-source is nonanoic acid, a $C_9$-homopolymer is produced that has no $C_7$.

In another aspect of the invention, a method of making MCL-PHA with a selected ratio of comonomers is provided. In some embodiments, substrate (i) is a fatty acid, which may be a functionalized fatty acid.

The MCL-PHAs obtained by these methods are polymers whose monomeric constituents are determined by the nature of the structurally-related carbon source, and whose monomeric compositions are determined according to the selected concentrations of the structurally-related carbon source, the β-oxidation inhibitor, and the structurally-unrelated carbon source. The melting point, degree of crystallinity, and rate of crystallinity, as well as other related physical and mechanical properties of the MCL-PHAs, are affected by the molar fraction of the longer chain comonomers.

For example, when octanoic acid, acrylic acid, and glucose were used in the method of the invention described herein, MCL-PHAs were obtained that were polymers of poly(3-OH-octanoate-co-3-OH-hexanoate) with a 3-OH-octanoate content of 88 mol % to 98 mol % and with a 3-OH-hexanoate content of 12 mol % to 2 mol %. Also, when nonanoic acid, acrylic acid, and glucose were used in the method of the invention described herein, MCL-PHAs were obtained that were polymers of poly(3-OH-nonanoate-co-3-OH-heptanoate) with a 3-OH-nonanoate content of 65 mol % to 96 mol % and with a 3-OH-heptanoate content of 35 mol % to 4 mole %. The average molecular weight was between 50,000 and 200,000 g mol$L^{-1}$, typically between 80,000 and 150,000 g mol$L^{-1}$. Glass transition temperatures ranged from −50° C. to −30° C. Melting temperatures (Tm) were 40° C. to 75° C. Young's modulus was up to 12 MPa. Tensile stress at maximum load was up to 16 MPa. Elongation at break was up to 1400%.

Referring to FIG. 1, a plot is shown of Absorbance at λ=650 nm for 12 h and 24 h cultures of *Pseudonomas putida* KT2440 grown in the presence of various initial concentrations of representative β-oxidation pathway inhibitor acrylic acid. As shown, cell growth was substantially affected by increasing the concentration of acrylic acid in shake flasks. An acrylic acid concentration of 0.2 g $L^{-1}$ reduced the absorbance by two fold. At acrylic acid concentrations of greater than 0.4 g $L^{-1}$ either weak growth or no growth was observed.

Figure 2:
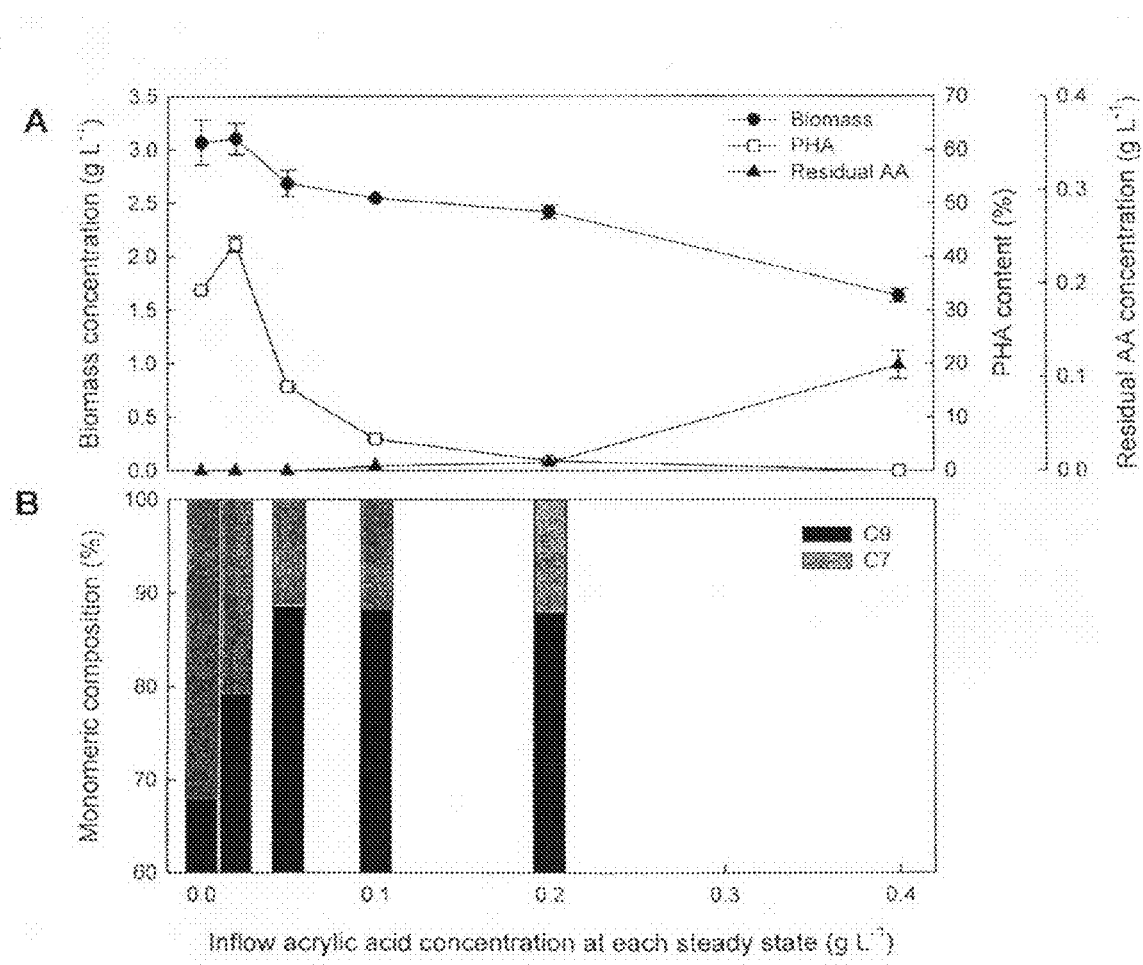
FIGS. 2A and 2B graphically show the effect of a β-oxidation pathway inhibitor on cell growth, PHA content (which in this case is PHN), and PHA composition for cultures grown by continuous fermentation at various inflow concentrations of acrylic acid with a feed containing nonanoic acid as sole carbon source. Samples were taken after systems had reached steady state as judged by attainment of stable rates of carbon dioxide production.

Referring to FIGS. 2A and 2B, plots are shown that graphically present the effect of a β-oxidation pathway inhibitor on cell growth, PHA (which in this case is PHN) content, and PHA composition for cultures grown at various inflow concentrations of acrylic acid with a single feeding of nonanoic acid in a continuous fermentation. Samples were taken after systems had reached steady state as judged by attainment of stable rates of carbon dioxide production. FIG. 2A is a plot of biomass concentration, PHA content, and residual acylic acid concentration versus inflow acrylic acid concentration. FIG. 2B is a plot of monomeric composition of isolated MCL-PHA ($C_9$ and $C_7$) versus inflow acrylic acid concentration. An acrylic acid as low as 0.02 g/L affected monomeric composition (see FIG. 2B). Biomass decreased slightly while the accumulated β-oxidation intermediates were diverted to PHA accumulation. At increased inhibitor concentration, the molar $C_9$ fraction of the PHA produced increased to about 90% but not further, indicating that inhibition of β-oxidation was incomplete. Above an inflow acrylic acid concentration of 0.02 g/L, both biomass concentration and PHA content decreased.

Figure 3:
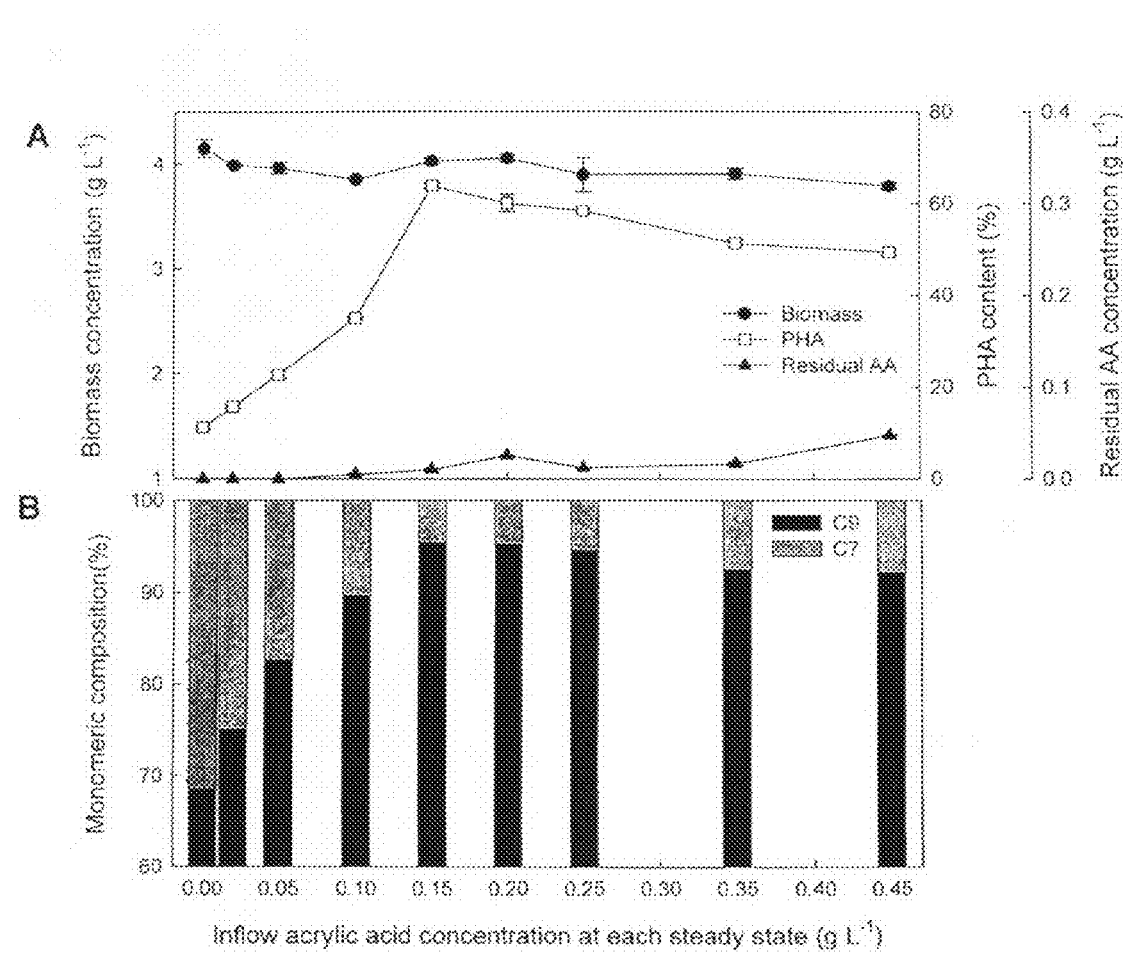
FIGS. 3A and 3B graphically show the effect of a β-oxidation pathway inhibitor on cell growth, PHA content (which in this case is PHN), and PHA composition for cultures grown at various inflow concentrations of acrylic acid with cofeeding of nonanoic acid and glucose in a continuous fermentation. Samples were taken after systems had reached steady state.

Referring to FIGS. 3A and 3B, plots are shown to demonstrate the effect of β-oxidation pathway inhibitor on cell growth, PHN content, and PHN composition for cultures grown at various concentrations of acrylic acid with cofeeding of nonanoic acid and glucose in a continuous fermentation. The sample point was taken once the system had reached steady state. FIG. 3A is a plot of biomass concentration, PHA (which in this case is PHN) content, and residual acrylic acid concentration versus inflow acrylic acid concentration. FIG. 3B is a plot of monomeric composition of isolated MCL-PHA ($C_9$ and $C_7$) versus inflow acrylic acid concentration. As described in Example 3, experiments were conducted to examine the effects of acrylic acid on cell growth and PHA production in carbon-limited chemostat culture with nonanoic acid and glucose cofeeding. Unlike when only nonanoic acid was fed, with cofeeding of nonanoic acid and glucose, the biomass concentration decreased very little and the intracellular PHN content increased from about 11 to 64% as inhibitor concentration increased from 0 to 0.15 g/L. The mole percentage of $C_9$ increased steadily from about 68 mol % to 96 mol %. In summary, FIG. 3B shows results of polymer syntheses with a 3-OH-nonanoate mol percent content of 68, 75, 83, 90, 92, 94, 95, and 96 mol % and corresponding 3-OH-heptanoate mole percentages.

Figure 4:
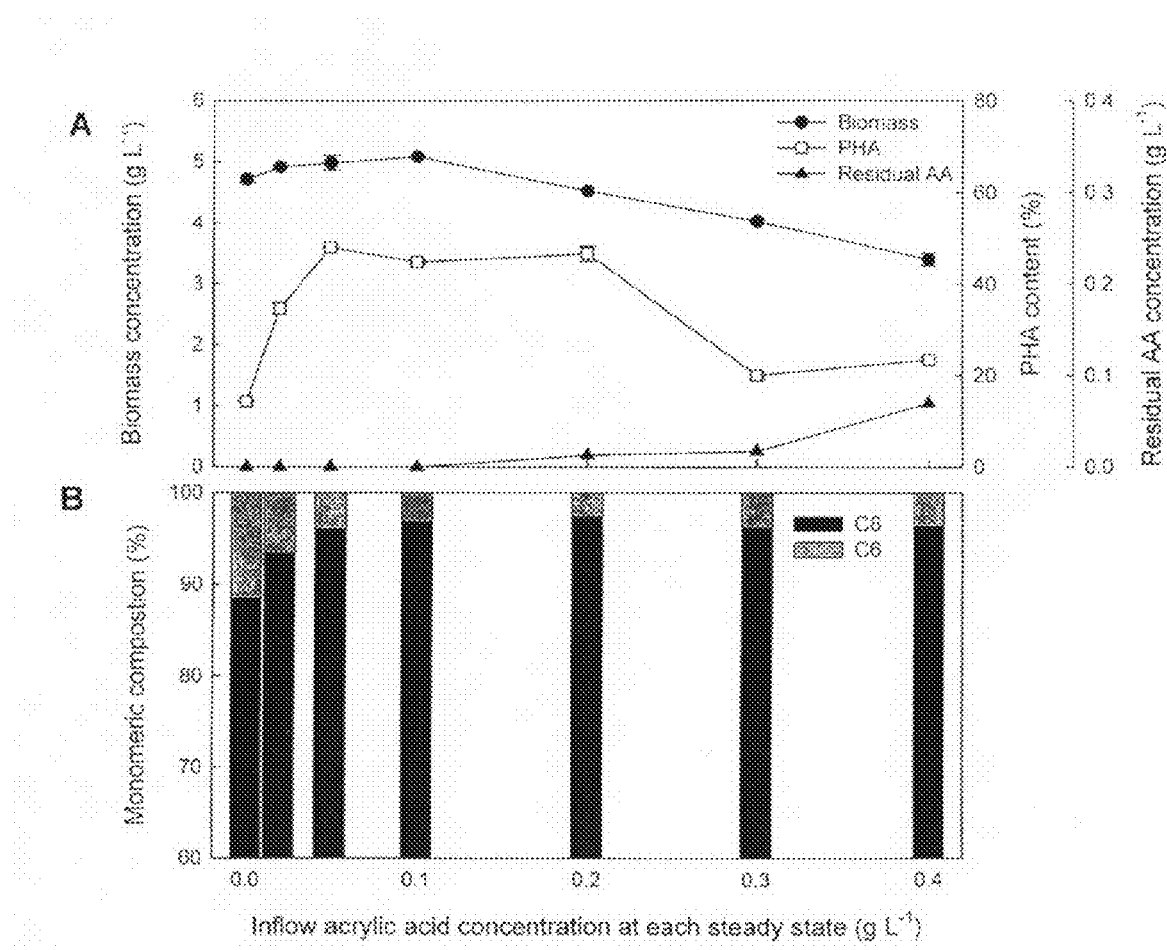
FIGS. 4A and 4B graphically show the effect of a β-oxidation pathway inhibitor on cell growth, PHA content (which in this case is PHO), and PHA composition for cultures grown at various inflow concentrations of acrylic acid with cofeeding of octanoic acid and glucose in a continuous fermentation. Samples were taken once systems had reached steady state.

Referring to FIGS. 4A and 4B, plots are shown to demonstrate the effect of β-oxidation pathway inhibitor on cell growth, PHO content, and PHO composition for cultures grown at various concentrations of acrylic acid with cofeeding of octanoic acid and glucose in a continuous fermentation. Samples were taken once steady state had been reached. FIG. 4A is a plot of biomass concentration, PHA (which in this case is PHO) content, and residual acrylic acid concentration versus inflow acrylic acid concentration. FIG. 4B is a plot of monomeric composition of isolated PHO($C_8$ and $C_6$) versus inflow acrylic acid concentration. As described in Example 4, experiments were conducted to examine the effects of acrylic acid on cell growth and PHA production in carbon-limited chemostat culture with octanoic acid and glucose cofeeding. The mole percentage of $C_8$ increased steadily from 88 mol % to 98 mol % with the increase in inflow acrylic acid concentration from 0 to 0.2 g/L. In summary, in FIG. 4B, results are shown for PHO samples having mole percentages of 88, 93, 96, 97, and 98 mol % 3-OH-octanoate content and a corresponding mole percentage of 3-OH-hexanoate content.

Figure 5:
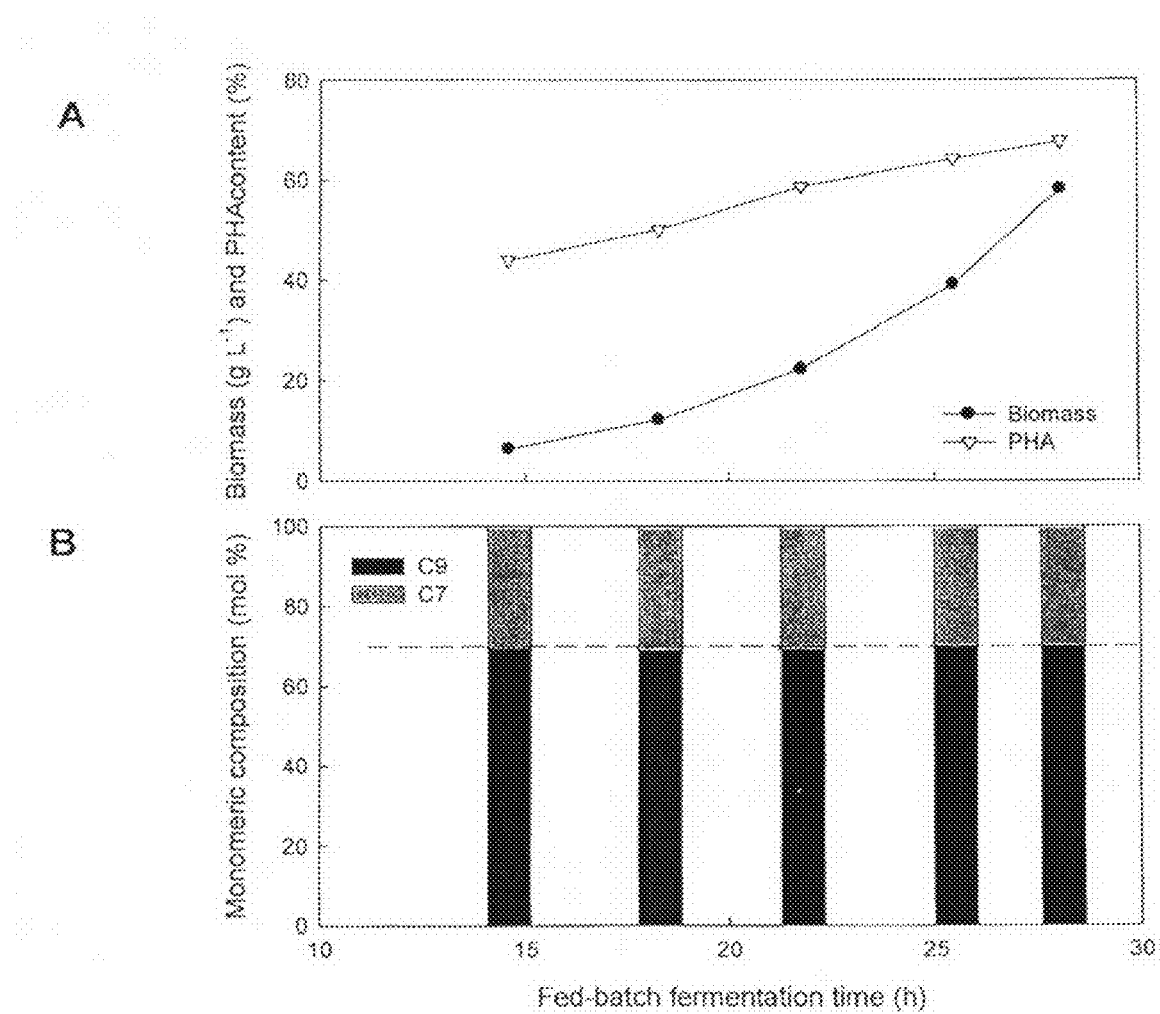
FIGS. 5A and 5B graphically show the time profile of biomass concentration, and PHA content (which in this case is PHN) (see FIG. 5A) and monomeric composition ($C_9$ and $C_7$) (see FIG. 5B) of isolated MCL-PHA during a fed-batch fermentation with co-feeding of nonanoic acid and glucose with a mass ratio of 1:1, and in the absence of acrylic acid.

Referring to FIGS. 5A and 5B, plots are shown of the time profile of biomass concentration, PHA (which in this case is PHN) content, and monomeric composition of isolated MCL-PHA ($C_9$ and $C_7$) during a fed-batch fermentation with cofeeding of nonanoic acid and glucose with a mass ratio of 1:1, and in the absence of acrylic acid. Fed-batch is the most commonly used bacterial fermentation technique (compared to batch mode and continuous mode fermentation) at industrial scale. Hence, as described in Example 5, an experiment was conducted to determine the feasibility of the cofeeding of structurally-related carbon source (nonanoic acid) and structurally-unrelated carbon source (glucose) method in such fermentation. As shown by the results, the monomeric composition of MCL-PHA produced was consistent at 69.5±0.4 mol % $C_9$ (3-OH-nonanoate) and the remaining comonomer was $C_7$ (3-OH-heptanoate) throughout the entire fermentation. Such MCL-PHA composition was also consistent with the composition obtained under similar cofeeding conditions during continuous fermentation, when β-oxidation pathway inhibitor (acrylic acid) was absent.

Figure 6:
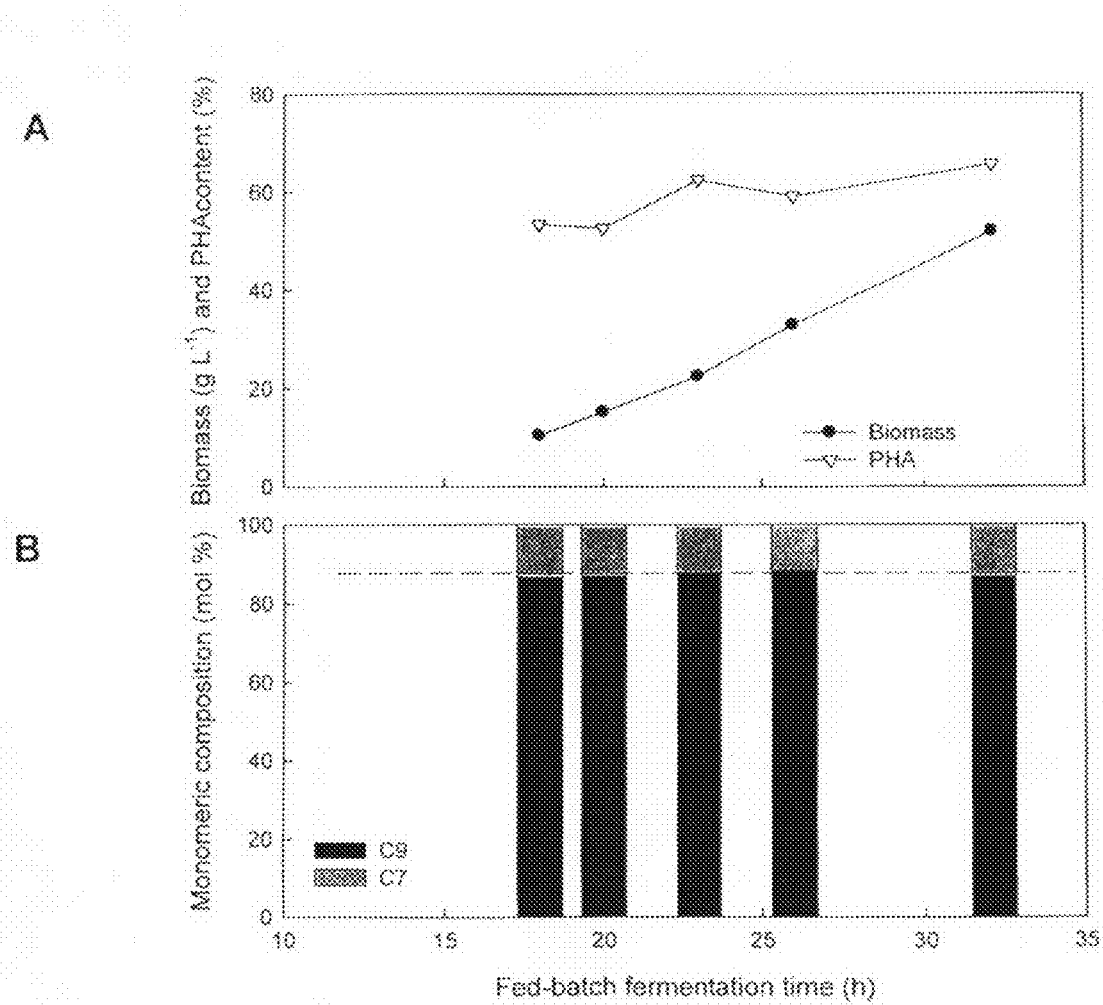
FIGS. 6A and 6B graphically show the time profile of biomass concentration, PHA content (which in this case is PHN) (see FIG. 6A) and monomeric composition of isolated MCL-PHA ($C_9$ and $C_7$) (see FIG. 6B) during a fed-batch fermentation with co-feeding of nonanoic acid, glucose, and acrylic acid at a mass ratio of 1.25:1:0.03.

Referring to FIGS. 6A and 6B, plots are shown of the time profile of biomass concentration, PHN content, and monomeric composition of isolated MCL-PHA ($C_9$ and $C_7$) during a fed-batch fermentation with cofeeding of nonanoic acid, glucose and acrylic acid with a mass ratio of 1.25:1:0.03. As described in example 6, an experiment was conducted to determine the feasibility of the cofeeding of structurally related carbon source (nonanoic acid), structurally-unrelated carbon source (glucose), and β-oxidation pathway inhibitor (acrylic acid) method in such fermentation. As shown in FIG. 6B, the monomeric composition of PHN was consistent throughout the entire fermentation at about 88% $C_9$ (3-OH-nonanoate) (by GC it was 87.8±0.8 mol %) and the remaining comonomer was $C_7$ (3-OH-heptanoate). Such significant change versus the previous figure demonstrated the effectiveness of β-oxidation pathway inhibitor in modulating the MCL-PHA monomeric composition in fed-batch fermentation.

Figure 7:
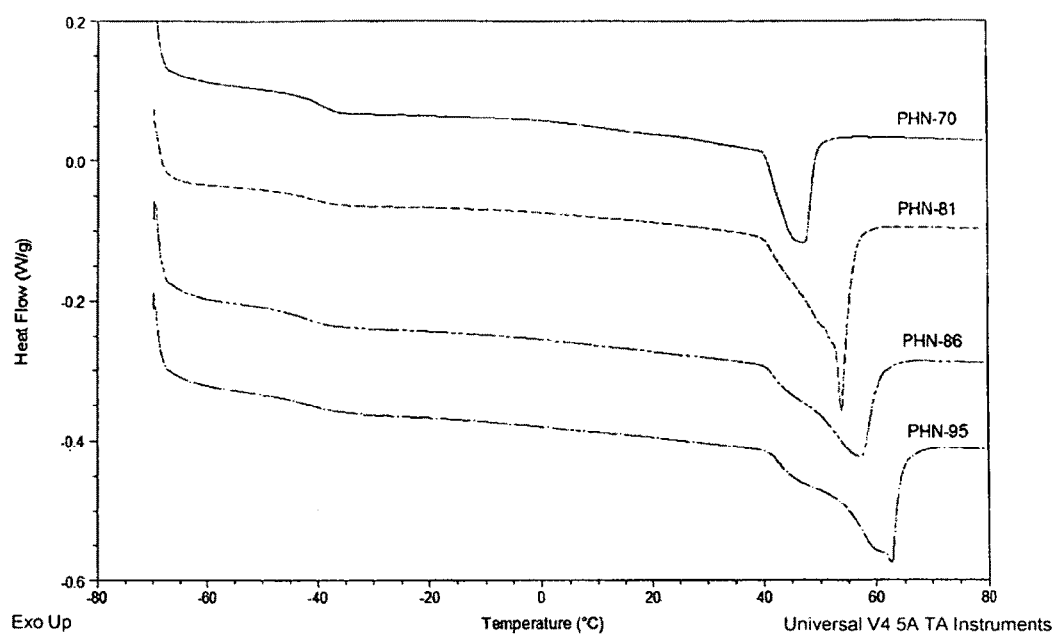
FIG. 7 is an overlay of the Differential Scanning Calorimetry (DSC) up-heating curves of various poly(3-OH-nonanoate-co-3-OH-heptanoate) compositions. PHN-70 is the abbreviation of poly(3-OH-nonanoate-co-3-OH-heptanoate) with 70 mol % nonanoate and 30 mol % heptanoate. PHN-81 is the abbreviation of poly(3-OH-nonanoate-co-3-OH-heptanoate) with 81 mol % nonanoate and 19 mol % heptanoate. PHN-86 is the abbreviation of poly(3-OH-nonanoate-co-3-OH-heptanoate) with 86 mol % nonanoate and 14 mol % heptanoate. PHN-95 is the abbreviation of poly(3-OH-nonanoate-co-3-OH-heptanoate) with 95 mol % nonanoate and 5 mol % heptanoate.

Referring to FIG. 7, the overlay of the Differential Scanning Calorimetry (DSC) up-heating curves of various poly(3-OH-nonanoate-co-3-OH-heptanoate) demonstrated a clear increase in material peak melting point associated with the change in monomeric compositions. PHN samples that were studied included PHN-70, PHN-81, PHN-86, and PHN-95.

Figure 8:
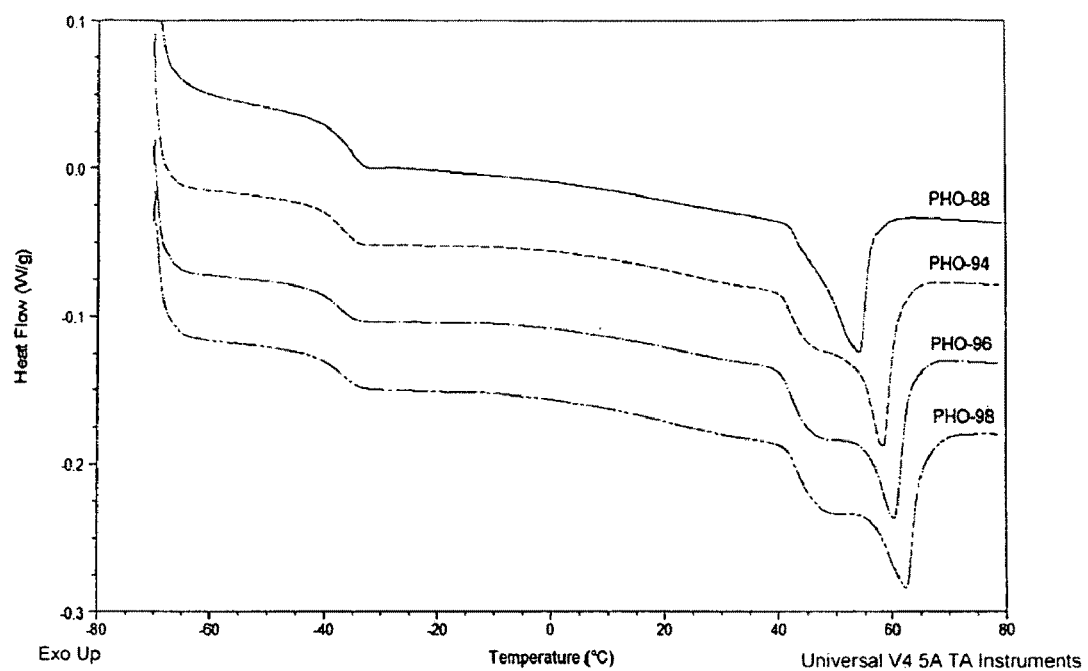
FIG. 8 is an overlay of the Differential Scanning Calorimetry (DSC) up-heating curves of various poly(3-OH-octanoate-co-3-OH-hexanoate) compositions. PHO-88 is the abbreviation of poly(3-OH-octanoate-co-3-OH-hexanoate) with 88 mol % octanoate and 12 mol % hexanoate. PHO-94 is the abbreviation of poly(3-OH-octanoate-co-3-OH-hexanoate) with 94 mol % octanoate and 6 mol % hexanoate. PHO-96 is the abbreviation of poly(3-OH-octanoate-co-3-OH-hexanoate) with 96 mol % octanoate and 4 mol % hexanoate. PHO-98 is the abbreviation of poly(3-OH-octanoate-co-3-OH-hexanoate) with 98 mol % octanoate and 2 mol % hexanoate.

Referring to FIG. 8, the overlay of the Differential Scanning Calorimetry (DSC) up-heating curves of various poly(3-OH-octanoate-co-3-OH-hexanoate) demonstrated a clear increase in material peak melting point associated with the change in monomeric compositions. PHO samples that were studied included PHO-88, PHO-94, PHO-96, and PHO-98.

Referring to FIG. 9, a schematic is shown of major pathways involved in MCL-PHA synthesis by pseudomonads (Adapted from Vanderleij F R, Witholt B (1995) Strategies for the sustainable production of new biodegradable polyesters in plants—a review. Canadian Journal of Microbiology 41:222-238). Confirmed or postulated enzymes of each step are numbered as follows: alkane hydroxylase (1); alcohol dehydrogenase (2); aldehyde dehydrogenase (3); thiokinase (4); acyl-CoA dehydrogenase (5); enoyl-CoA hydratase or crotonase, (6); (S)-3-OH-acyl-CoA dehydrogenase (7); 3-ketoacyl-CoA thiolase (8); enoyl-CoA hydratase (9); 3-OH-acyl-CoA epimerase (10); ketoacyl-CoA reductase (11); PHA polymerase (12); (R)-3-OH-acyl (ACP-CoA) transferase (13); 3-OH-acyl-ACP dehydratase (14); enoyl-ACP reductase (15); fatty acid thioesterase (16); 3-ketoacyl synthase (17); ketoacyl-ACP dehydratase (18); ketoacyl-ACP synthase (19); and acetyl-CoA carboxyltransferase and malonyl-CoA ACP transacylase (20).

Figure 10:
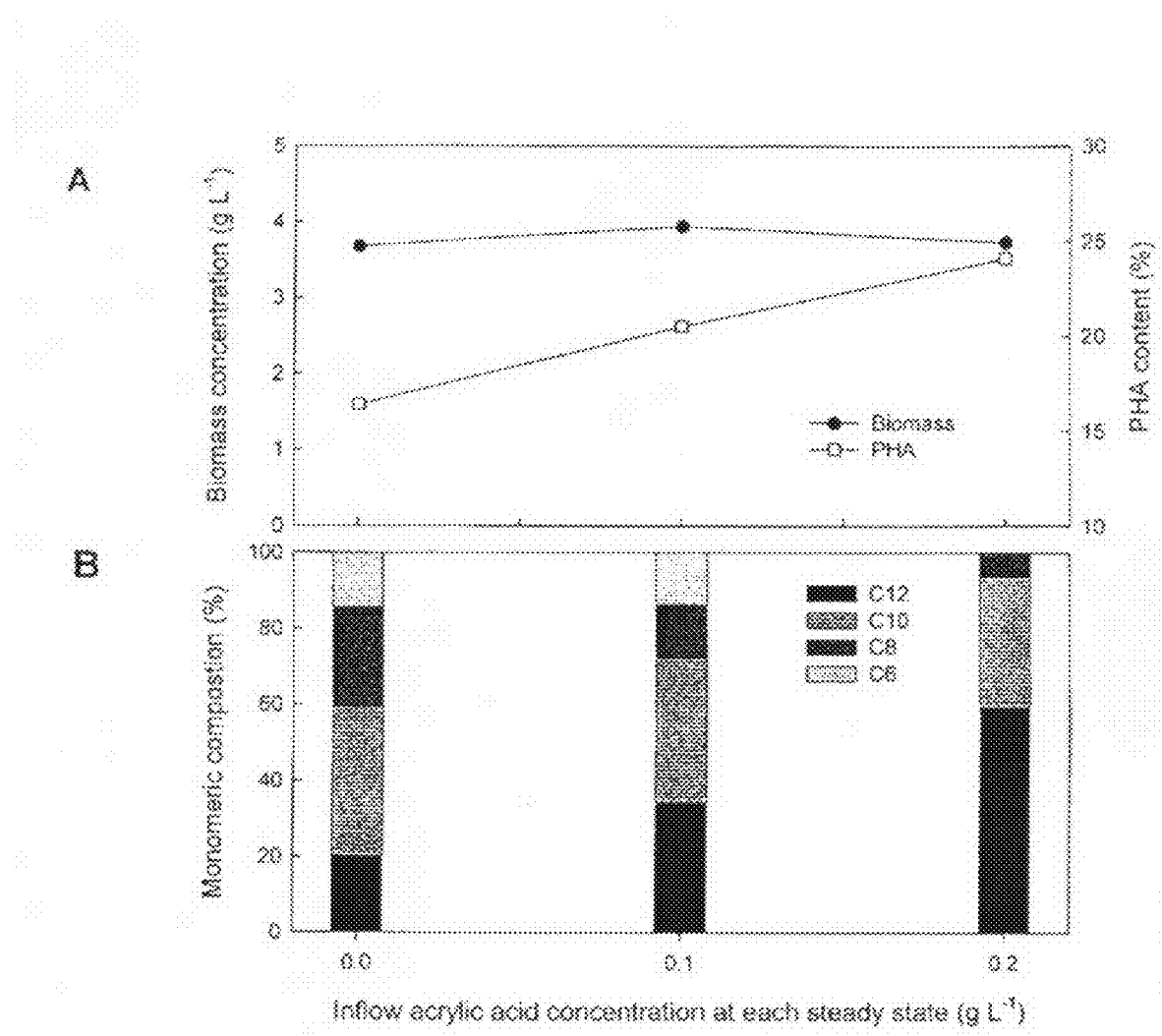
FIGS. 10A and 10B graphically show the effect of a β-oxidation pathway inhibitor on cell growth, PHA content, and PHA composition for cultures grown at various inflow concentrations of acrylic acid with cofeeding of dodecanoic acid and glucose in a continuous fermentation. Samples were taken once systems had reached steady state.

Referring to FIGS. 10A and B, plots are shown to demonstrate the effect of β-oxidation pathway inhibitor on cell growth, monomer content, and polymer composition for cultures grown at various concentrations of acrylic acid with cofeeding of dodecanoic acid and glucose in a continuous fermentation. Samples were taken once steady state had been reached. FIG. 10A is a plot of biomass concentration and PHA content versus inflow acrylic acid concentration. FIG. 10B is a plot of monomeric composition of isolated PHA ($C_{12}$, $C_{10}$, $C_8$ and $C_6$) versus inflow acrylic acid concentration. As described in Example 10, experiments were conducted to examine the effects of acrylic acid on cell growth and PHA production in carbon-limited chemostat culture with dodecanoic acid and glucose cofeeding. The mole percentage of $C_{12}$ increased steadily from 20 mol % to 60 mol % with the increase in inflow acrylic acid concentration from 0 to 0.2 g/L. In FIG. 10B, results are shown for PHA samples having mole percentages of 20, 35, 60 mol % 3-OH-dodecanoate content and corresponding mole percentages of 3-OH-decanoate, 3-OH-octanoate, and 3-OH-hexanoate content.

WORKING EXAMPLES

Materials and Methods

A basic glucose-only shake flask medium was a 100 mL liquid medium in a 500 mL Erlenmeyer flask. The medium comprised (g L$^{-1}$): $(NH_4)_2SO_4$ (4.70), $MgSO_4.7H_2O$ (0.80), $Na_2HPO_4.7H_2O$ (12.0), $KH_2PO_4$ (2.70), glucose (9.0), nutrient broth (1.0).

Continuous fermentations were carried out in a 1.5 L stirred tank bioreactor (Bioflo IIc, New Brunswick Scientific, N.J., USA) with a working volume of 1.1 L. The fermentor was operated at 28.5±1° C. and the pH was automatically controlled at 6.85±0.05 using 2 N potassium hydroxide solution. The dissolved oxygen was monitored with an Ingold polarographic probe (available from Mettler-Toledo Ingold Inc., Bedford, Mass., USA) and maintained no lower than 30% air saturation with an aeration rate of 0.8 vvm (void volumes per minute) and an agitation speed up to 900 rpm. Nonanoic acid was fed separately at controlled speed by a peristaltic nutrient pump on the bioreactor. All other aqueous medium was mixed and fed together. The dilution rate of all continuous fermentations was controlled at 0.25$^{-1}$ by fixing the working volume and a constant aqueous medium feeding rate.

Fed-batch fermentations were conducted in a 5 L stirred tank bioreactor with 3 L working volume (Minifors, INFORS HT, Bottmingen, Switzerland). The specific growth rate was controlled at 0.25 h$^{-1}$ or 0.15 h$^{-1}$ by exponentially feeding the carbon sources as growth-limiting nutrients. β-oxidation inhibitor was added with the glucose feeding solution at a fixed mass as specified in the related examples. Other nutrients were added at the beginning of the fermentation at the following concentrations (g/L): $(NH_4)_2SO_4$ (4.70), $MgSO_4.7H_2O$ (0.80), $Na_2HPO_4.7H_2O$ (18.0), $KH_2PO_4$ (4.05), trace element solution (10 mL/L). pH was controlled by adding a 28% ammonia solution, which also served as nitrogen source.

During shake flask, batch, fed-batch, or continuous cultivations, fermentation broth samples were taken. Known amounts of such broths were centrifuged to obtain the medium's supernatant and concentrated biomass. The biomasses were washed with distilled water, centrifuged again, re-suspended, frozen, and lyophilized to obtain dried biomass. The supernatant was used to analyze carbon source, inhibitor, and nutrient concentration. The dried biomass was used to obtain the cell concentration, cellular PHA content and composition.

Dried samples were weighed to obtain dry biomass amounts. PHA content and composition were determined by gas chromatographic method as described below (Sun, Z., et al. (2007). *Appl. Microbiol. Biotechnol.*, 74:69). A PHA standard was prepared by acetone extraction and methanol precipitation, followed by three cycles of the same extraction and precipitation procedures (see Jiang, X., et al. (2006) *J. Microbial. Methods* 67:212-219).

Recovery of intracellular MCL-PHA from microorganisms is possible using one of many procedures published in the academic and patent literature (e.g., solvent extraction of PHA, enzymatic digestion of non-PHA cellular material, chemical digestion of non-PHA cellular material). In the studies described herein, a solvent extraction method (Jiang et al. 2007. *J. Microbiological Methods*) was used in recovering the PHA. In certain embodiments, separation and/or isolation optionally including purification of the polymer is preferred. However, in other embodiments, it is not necessary to separate the polymer from the microbial cells. Rather, it is possible in some applications to use the microbial cells grown according to methods of the present invention as a source of polymer wherein cellular material is diluted and/or destroyed in subsequent process steps.

Known amount of dried biomass, or purified MCL-PHA, or MCL-PHA standard with known composition and elution time of each of its components, were reacted in 2 mL chloroform plus 1 mL methanol containing 15% (v/v) concentrated sulfuric acid as acidifying agent and 0.2% (w/v) benzoic acid as internal standard, at 100° C. for 4 hours. After the reaction, 1 mL distilled water was added and the sample was mixed vigorously by vortex mixer for 1 min and phase separation was allowed to take place. 1 mL of the chloroform phase was taken for gas chromatography analysis using a CP3900 Varian GC equipped with Split/Splitless Injector and Flame Ionization Detector (FID). The injection volume was 1 μL and split ratio was 20. The injector temperature was 250° C. and the FID at 275° C. The oven heating profile was: initial 90° C. for 0.5 min, 5° C./min to 95° C. and held for 0.5 min, 30° C./min to 170° C. and held for 2.5 min. Methyl-3-hydroxyalkanoate was identified and its molar amount was calculated by comparing peak area to the corresponding peak of known methyl-3-hydroxyalkanoate generated from known MCL-PHA standard, which was characterized by NMR and GC/MS.

The weight average molecular weight (Mw) and number average molecular weight (Mn) of the MCL-PHA prepared in distilled tetrahydrofuran (THF) were analyzed at 40° C. using a Waters 2695 Gel Permeation Chromatograph (GPC) equipped with four Styragel columns of pore sizes 100, 500, 103, and 104 Å coupled to a Waters 410 differential refractive index detector. THF was the mobile phase at 1 mL/min, and polystyrene was used as a standard.

Differential scanning calorimetry (DSC) analysis was performed to obtain glass transition temperature ($T_g$), melting temperature ($T_m$), and relative crystallinity expressed as heat of fusion ($\Delta H$), using TA Instruments DSC Q100 (available from TA Instruments, New Castle, Del., USA). Purified MCL-PHA samples were melted at 70° C. and allowed to crystallize at 25° C. for 5 days before being analyzed. During the analysis, a sample of known mass was placed in a special aluminum pan and sealed. The sample was first heated from −70° C. up to 80° C. at a rate of 10° C./min. During this heating, an endothermic peak was observed and the temperature value at the peak point was taken as the $T_m$. The sample was held at 80° C. for 5 min. before it was cooled down to −70° C. at 10° C./min rate. It was then held at −70° C. for 5 min and heated again to 80° C. at 10° C./min. The onset $T_g$ was obtained from the second heating cycle.

Example 1

Effect of Acrylic Acid on Cell Growth in the Presence of Glucose as Carbon Source The effect of acrylic acid on cell growth was determined using *Pseudomonas putida* KT2440 (ATCC 47054). *Pseudomonas putida* KT2440 (ATCC 47054) was maintained on nutrient agar plates at 4° C. before inoculation. The toxicity of a β-oxidation inhibitor, acrylic acid, to the growth of *Pseudomonas putida* KT2440 was determined by shake flask experiment. The cultivation conditions were 28° C. in a New Brunswick Shaker-Incubator at 200 rpm. The medium used was the basic glucose-only shake flask medium described above, plus appropriate amount of acrylic acid.

500 mL Erlenmeyer flasks were used with each containing 100 mL of medium. In addition to the basic medium described above, increasing concentrations of acrylic acid (AA) at 0, 0.2, 0.4, 0.8, 2.0 g/L were prepared in each flask. The first set of such flasks was cultured for 12 h and the second set of such flasks was cultured for 24 h. After the specified culturing time, a sample was taken to measure the absorbance at 650 nm in the spectrophotometer. Data obtained from these studies are presented in FIG. 1. The results demonstrated that cell growth can be affected by increased concentration of acrylic acid in the culture medium.

Example 2

Preparation of MCL-PHAs with Controlled Composition Prepared in the Presence of a β-oxidation Inhibitor Using Continuous Fermentation MCL-PHAs with controlled composition were produced in continuous fermentation of *Pseudomonas putida* KT2440 by increasing the concentration of acrylic acid. The inoculum was grown in the basic glucose medium described above. After 18 h of cultivation, 200 mL of such culture was inoculated into a 1.5 L bioreactor with 1.1 L working volume (Bioflo II, New Brunswick Scientific, N.J., USA). The bioreactor was then operated in continuous fermentation mode with a medium dilution rate of $0.25^{-1}$. The inflow medium was composed of the following components (per liter): carbon source, nonanoic acid (3.80 g±0.1 g for each steady state); β-oxidation inhibitor, acrylic acid (0, 0.02, 0.05, 0.10, 0.20 g for each steady state); nutrients $(NH_4)_2SO_4$ (5.02 g); $MgSO_4.7H_2O$ (1.03 g); $Na_2HPO_4.7H_2O$ (2.24 g); $KH_2PO_4$ (0.50 g); and trace element solution (1.40 mL). The trace element solution was composed of the following components (per liter): $FeSO_4.7H_2O$ (10.00 g); $CaCl_2.2H_2O$ (3.00 g); $ZnSO_4.7H_2O$ (2.20 g); $MnSO_4.4H_2O$ (0.50 g); $H_3BO_3$ (0.30 g); $CoCl_2.6H_2O$ (0.20 g); $Na_2MoO_4.2H_2O$ (0.15 g); $NiCl_2.6H_2O$ (0.02 g); and $CuSO_4.5H_2O$ (1.00 g).

Five different bacterial physiological steady states were established at each acrylic acid increment by allowing at least 5 reactor working volumes of medium flow through the bioreactor and by monitoring the carbon dioxide production rate to reach constant value. Sample was then taken at such steady state and analyzed. See the data from these studies in FIGS. 2A and 2B.

The results demonstrated that by providing acrylic acid as β-oxidation inhibitor, MCL-PHAs obtained from nonanoic acid as the only carbon source were always composed of $C_9$ (3-OH-nonanoate) and $C_7$ (3-OH-heptanoate) monomers but their relative fraction could be controlled by increasing inhibitor concentration. However, since inhibiting the β-oxidation pathway also means inhibiting energy generation, PHA accumulation was greatly affected when nonanoic acid was the only carbon source. At acrylic acid level of 0.2 g $L^{-1}$, very little PHA content could be achieved.

Example 3

Preparation of MCL-PHAs with Controlled Composition Prepared in the Presence of a Structurally-related Carbon Source (Nonanoic Acid), a Structurally-unrelated Carbon Source (Glucose), and Increasing Concentration of β-oxidation Inhibitor (Acrylic Acid) Using Continuous Fermentation MCL-PHAs with controlled composition were produced in continuous fermentation of *Pseudomonas putida* KT2440 by providing both nonanoic acid and glucose as carbon sources, and by increasing the concentration of acrylic acid. The operation of the continuous fermentations was similar to that described in Example 2. The inflow medium was composed of the following components (per liter): carbon source, nonanoic acid (2.90±0.15 g for each steady state); glucose (3.90 g for each steady state); β-oxidation inhibitor acrylic acid (0, 0.02, 0.05, 0.10, 0.20 g for each steady state); nutrients; and trace element solution (1.40 mL). The nutrients included: $(NH_4)_2SO_4$ (5.02 g); $MgSO_4.7H_2O$ (1.03 g); $Na_2HPO_4.7H_2O$ (2.24 g); and $KH_2PO_4$ (0.50 g). Steady state results were obtained as presented in FIGS. 3A and 3B.

The results demonstrated that, by providing both a structurally-related carbon source such as nonanoic acid and a structurally-unrelated carbon source such as glucose, and by providing acrylic acid as β-oxidation inhibitor, the MCL-PHA monomeric composition could be controlled without sacrificing PHA content and PHA production.

Example 4

Preparation of MCL-PHAs with Controlled Composition Prepared in the Presence of a Structurally-related Carbon Source (Octanoic Acid), a Structurally-unrelated Carbon Source (Glucose), and Increasing Concentration of β-oxidation Inhibitor (Acrylic Acid) Using Continuous Fermentation MCL-PHAs with controlled composition were produced in continuous fermentation of *Pseudomonas putida* KT2440 by providing both octanoic acid and glucose as carbon source, and by increasing the concentration of acrylic acid.

The operation of continuous fermentations was similar to that described in Example 2. The inflow medium was composed of the following components (per liter): carbon source, octanoic acid (3.60 g±0.16 g for each steady state); glucose (3.90 g for each steady state); β-oxidation inhibitor acrylic acid (0, 0.02, 0.05, 0.10, 0.20 g for each steady state); nutrients; and trace element solution (1.40 mL). The nutrients included $(NH_4)_2SO_4$ (5.02 g); $MgSO_4.7H_2O$ (1.03 g); $Na_2HPO_4.7H_2O$ (2.24 g); and $KH_2PO_4$ (0.50 g). Steady state results were obtained as presented in FIGS. 4A and 4B.

The results demonstrated that, by providing both a structurally-related carbon source such as octanoic acid and a structurally-unrelated carbon source such as glucose, and by providing acrylic acid as β-oxidation inhibitor, the MCL-PHA monomeric composition could be controlled without sacrificing PHA content.

Example 5

Preparation of MCL-PHAs with Controlled Composition Prepared in the Presence of a Structurally-related Carbon Source (Nonanoic Acid) and a Structurally-unrelated Carbon Source (Glucose), and in the Absence of β-oxidation Inhibitor (Acrylic Acid) Using Fed-batch Fermentation MCL-PHA was produced in fed-batch fermentation by providing nonanoic acid as MCL-PHA-generating carbon source and glucose as energy-providing carbon source, without providing acrylic acid as β-oxidation inhibitor. The inoculum was grown in the basic glucose medium described above. After 18 h of cultivation, 300 mL of such culture was inoculated into a 5 L bioreactor with 3 L working volume (Minifors, INFORS HT, Bottmingen, Switzerland). The fermentation was then operated at fed-batch mode with programmed nonanoic acid and glucose feeding rate that controlled the culture specific growth rate at $0.25^{-1}$. The medium was composed of the following components (per liter): nonanoic acid and glucose (1:1 (w/w) fed at a programmed rate); nutrients; and trace element solution (10.00 mL). Nutrients included $(NH_4)_2SO_4$ (4.70 g); $MgSO_4.7H_2O$ (0.80 g); $Na_2HPO_4.7H_2O$ (12.00 g); and $KH_2PO_4$ (2.70 g). The fermentation was operated at 28° C. and the pH was controlled by feeding ammonium water. Results that were obtained after 28 hours fermentation are presented in FIGS. 5A and 5B. The results demonstrated that with no β-oxidation inhibitor (i.e., no acrylic acid), the monomeric composition of MCL-PHA in the microorganism was consistent at 69.5±0.4 mol % $C_9$ (3-OH-nonanoate) and the remaining comonomer was $C_7$ (3-OH-heptanoate), as indicated by the dashed line.

Example 6

Preparation of MCL-PHAs with Controlled Composition Prepared in a Fed-batch Fermentation in the Presence of a Structurally-related Carbon Source (Nonanoic Acid), a Structurally-Unrelated Carbon Source (Glucose), and β-oxidation Inhibitor (Acrylic Acid) Using Fed-batch Fermentation MCL-PHA with controlled composition was produced in fed-batch fermentation by providing nonanoic acid as MCL-PHA-generating carbon source and glucose as energy-providing carbon source, and by providing acrylic acid as β-oxidation inhibitor. The setup of the fermentation was similar to that of Example 5. The weight ratio of nonanoic acid, glucose and acrylic acid in the feeding was 1.25:1:0.03. The bioreactor was operated in fed-batch fermentation mode with programmed carbon source feeding rate such that the culture specific growth rate was 0.15 $h^{-1}$.

The medium was composed of the following components (per liter): nonanoic acid, glucose and β-oxidation inhibitor acrylic acid were all fed at programmed rate at the following ratio, nonanoic acid:glucose:acrylic acid=1.25:1:0.03 (w/w/w); nutrients and trace element solution (10.00 mL). The nutrients included: $(NH_4)_2SO_4$ (4.70 g); $MgSO_4.7H_2O$ (0.80 g); $Na_2HPO_4.7H_2O$ (12.00 g); and $KH_2PO_4$ (2.70 g). Results obtained after 32 hours fermentation (see FIG. 6) were consistent during the fermentation at 87.8±0.8 mol % $C_9$ (3-OH-nonanoate) and the remaining comonomer was $C_7$ (3-OH-heptanoate), as indicated by the dashed line. The results demonstrated that with acrylic acid present as β-oxidation inhibitor, the monomeric composition of MCL-PHA in the microorganism was changed from the product in the absence of a β-oxidation inhibitor, as discussed in Example 5.

Example 7

Thermal Property Determination of Poly(3-Oh-nonanoate-go-3-OH-heptanoate) with Controlled Monomeric Composition Poly(3-OH-nonanoate-co-3-OH-heptanoate) (PHN) of varied monomeric compositions were produced by methods described in Example 3. After the MCL-PHA samples were purified and annealed for certain period of time, the samples' melting behavior was recorded using Differential Scanning calorimetry (DSC) with a heating profile from −70° C. to 80° C. at 5° C. per min. Results are presented as up-heating curves, which are overlaid in FIG. 7. PHN-70 is the abbreviation of poly(3-OH-nonanoate-co-3-OH-heptanoate) with 70 mol % nonanoate and 30 mol % heptanoate. A clear increase in melting temperature (Tm, ° C.) of the series PHN with the increase of 3-hydroxy-nonanoate (HN) content was demonstrated by these data.

Example 8

Thermal Property Determination of Poly(3-OH-octanoate-co-3-OH-hexanoate) with Controlled Monomeric Composition Poly(3-OH-octanoate-co-3-OH-hexanoate) (PHO) of varied monomeric compositions were produced by methods described in Example 4. After the MCL-PHA samples were purified and annealed for certain period of time, their melting behavior was recorded using Differential Scanning Calorimetry (DSC). The heating profile was from −70° C. to 80° C. at 5° C. per min. The up-heating curves are overlaid in FIG. 8. PHO-88 is the abbreviation of poly(3-OH-octanoate-co-3-OH-hexanoate) with 88 mol % octanoate and 12 mol % hexanoate. A clear increase in melting temperature (Tm, ° C.) of the series PHO with the increase of 3-hydroxy-octanoate (HO) content was demonstrated by these data.

Example 9

Stress-strain Measurements of Various PHN and PHO Samples

A series of PHN and PHO of varied monomeric compositions was produced using methods described previously. Sheets of the materials were prepared by melting each material on a glass surface in an oven at 10° C. above its melting temperature for certain period of time until a flat sheet was formed without visible air bubbles. Melted samples were then pressed with a Teflon sheet and kept pressed at room temperature for a certain period of time until the sample sheet could be peeled off the glass surface without being deformed significantly. This period of time was recorded as the annealing time of the sample. Such sample sheets were then used to produce dumbbell-shaped specimens according to ASTM D638 Type V dimension (American Society for Testing and Materials International (ASTM) Standard D638, 2004, "Standard Test Method for Tensile Properties of Plastics," ASTM International, West Conshohocken, Pa., 2004, DOI: 10.1520/C0033-03, www.astm.org.). The width of the narrow part of the sample was about 3.3 mm, while the thickness depended on the thickness of the original sample sheet, which was between 1.3 mm and 2.7 mm. Stress-strain measurements of these dumbbell-shaped specimens were obtained using a tensile testing instrument (model Instron 3369, available from Instron, Norwood, Mass., USA). The Instron tensile test used a crosshead speed of 100 mm per min. Properties such as annealing time (h), tensile stress at maximum load (MPa), Young's modulus (MPa), and extension at break (%) of various samples are summarized in Table 2.

As shown by the data in Table 2, the maximum tensile stress and Young's modulus of either PHN or PHO material can be increased significantly by increasing the molar content of HN or HO, respectively, without sacrificing their excellent elongation-to-break property.

Example 10

Preparation of MCL-PHAs with Controlled Composition Prepared in the Presence of a Structurally-related Carbon Source (Dodecanoic Acid), a Structurally-unrelated Carbon Source (Glucose), and Increasing Concentration of β-oxidation Inhibitor (Acrylic Acid) Using Continuous Fermentation MCL-PHAs with controlled composition were produced in continuous fermentation of *Pseudomonas putida* KT2440 by providing both dodecanoic acid and glucose as carbon source, and by increasing the concentration of acrylic acid.

The operation of continuous fermentations was similar to that described in Example 2. The inflow medium had the following components (per liter): carbon source, dodecanoic acid (1.14 g for each steady state); glucose (3.00 g for each steady state); β-oxidation inhibitor acrylic acid (0, 0.10, 0.20 g for each steady state); nutrients; and trace element solution (1.40 mL). The nutrients included $(NH_4)_2SO_4$ (5.02 g); $MgSO_4.7H_2O$ (1.03 g); $Na_2HPO_4.7H_2O$ (2.24 g); and $KH_2PO_4$ (0.50 g). Steady state results were obtained as presented in FIGS. 10A and 10B.

Results demonstrated that, by providing both a structurally-related carbon source such as dodecanoic acid and a structurally-unrelated carbon source such as glucose, and by providing acrylic acid as β-oxidation inhibitor, MCL-PHA monomeric composition could be controlled. As the inlet concentration of acrylic acid was increased from 0 to 0.1 to 0.2 g $L^{-1}$, molar C12 content increased from 20.4% to 34.5% to 59%.

Example 11

Preparation of MCL-PHAs with Controlled Composition Prepared in the Presence of a Structurally-related Carbon Source (Nonanoic Acid), a Structurally-unrelated Carbon Source (Glucose), and Increasing Concentration of β-oxidation Inhibitor (Acrylic Acid) Using Continuous Fermentation MCL-PHAs with controlled composition were produced in continuous fermentation of *Pseudomonas citronellolis*

DSM 50332 (ATCC 13674) by providing both nonanoic acid and glucose as carbon source, and by increasing the concentration of acrylic acid.

The operation of continuous fermentations was similar to that described in Example 2. The inflow concentration of β-oxidation inhibitor acrylic acid was varied to be 0, 0.01, 0.02, 0.025, 0.030, 0.035, 0.040 g for each steady state. The MCL-PHAs synthesized at any steady state comprised 3-OH-nonanoate and 3-OH-heptanoate ($C_9$ and $C_7$). Notably, the amount of 3-OH-nonanoate in the MCL-PHA product was successfully controlled. Compositions comprising from 65 mole % to 76 mole % 3-OH-nonanoate were obtained for the range of acrylic acid tested, with the remaining mole % being 3-OH-heptanoate.

It will be understood by those skilled in the art that this description is made with reference to certain preferred embodiments and that it is possible to make other embodiments employing the principles of the invention which fall within its spirit and scope as defined by the claims.

References

Diard, S.; Cartier, J. P.; Ageron, E.; Grimont, P. A. D.; Langlois, V.; Guerin, P.; Bouvet, O. M. M.; (2002) "Accumulation of poly(3-hydroxybutyrate) from octanoate, in different *Pseudomonas* belonging to the rRNA homology group I." *Syst. Appl. Microbiol.* 25:183-188.

Jiang, X.; Ramsay, J. A.; Ramsay, B. A.; (2006) "Acetone extraction of mcl-PHA from *Pseudomonas putida* KT2440." *J. Microbiol. Methods* 67:212-219.

Lee, S. Y.; Wong, H. H.; Choi, J. I.; Lee, S. H.; Lee, S. C.; Han, C. S.; (2000) "Production of medium-chain-length polyhydroxyalkanoates by high-cell-density cultivation of *Pseudomonas putida* under phosphorus limitation." *Biotechnol. Bioeng.* 68:466-470.

Ouyang, S.; Luo, R. C.; Chen, S.; Liu, Q.; Chung, A.; Wu, Q.; Chen, G.; (2007) "Production of polyhydroxyalkanoates with high 3-hydroxydodecanoate monomer content by fadB and fadA knockout mutant of *Pseudomonas putida* KT2442." *Biomacromolecules* 8:2504-2511.

Park, S. J.; Park, J. P.; Lee, S. Y.; Doi, Y.; (2003) "Enrichment of specific monomer in medium-chain-length poly(3-hydroxyalkanoates) by amplification of fadD and fadE genes in recombinant *Escherichia coli*." *Enzyme Microb. Technol.* 33:62-70.

Sanchez, R. J.; Schripsema, J.; da Silva, L. F.; Taciro, M. K.; Pradella, J. G. C.; Gomez, J. G. C. (2003) "Medium-chain-length polyhydroxyalkanoic acids (PHA(mcl)) produced by *Pseudomonas putida* IPT 046 from renewable sources." *European Polymer Journal* 39:1385-1394.

Sun, Z.; Ramsay, J. A.; Guay, M.; Ramsay, B. A.; (2007) "Carbon-limited fed-batch production of medium-chain-length polyhydroxyalkanoates from nonanoic acid by *Pseudomonas putida* KT2440." *Appl. Microbiol. Biotechnol.* 74:69.

U.S. Pat. No. 5,296,362

U.S. Pat. No. 7,169,598

TABLE 1

Generic structural formulae of polyhydroxyalkanoate copolymers and examples of monomers suitable for incorporation therein.

General structure of PHA, where $R^1$ and $R^2$ are side chains, and where x and y each represent a number that is the amount of a monomer in a macromolecule (e.g., polymer), and therefore they typically are very large numbers.

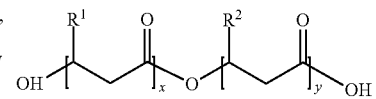

3-hydroxy-hexanoate (HHx) ("$C_6$")

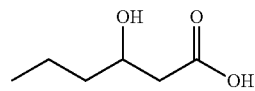

3-hydroxy-hepanoic acid (HHp) ("$C_7$")

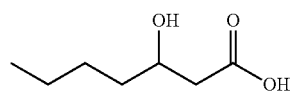

3-hydroxy-octanoic acid (HO) ("$C_8$")

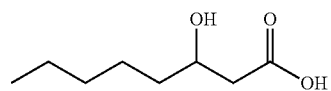

3-hydroxy-nonanoic acid (HN) ("$C_9$")

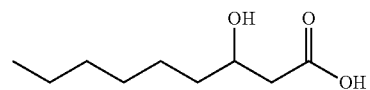

3-hydroxy-decanoic acid (HD) ("$C_{10}$")

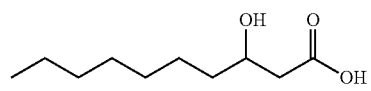

3-hydroxy-undecanoic acid (HUD) ("$C_{11}$")

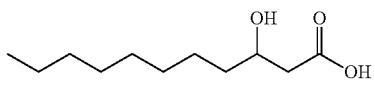

3-hydroxy-dodecanoic acid (HDD) ("$C_{12}$")

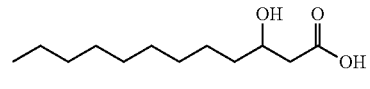

TABLE 2

Stress-strain measurements of monomeric compositions of PHN and PHO

| Sample | Annealing time at room temp. (h) | Thickness (mm) | Tensile stress at maximum load (MPa) | Young's modulus (MPa) | Elongation at break (%) |
|---|---|---|---|---|---|
| PHN-70 | 96 | 2.64 ± 0.01 | 6.7 ± 0.6 | 1.5 ± 0.1 | 1330 ± 30 |
| PHN-85 | 60 | 1.88 ± 0.01 | 10.7 ± 0.2 | 5.4 ± 0.4 | 1260 ± 30 |
| PHN-90 | 18 | 1.55 ± 0.20 | 11.4 ± 0.9 | 6.5 ± 1.2 | 1220 ± 20 |
| PHN-95 | 18 | 1.47 ± 0.03 | 15.5 ± 0.9 | 11.4 ± 1.3 | 1320 ± 80 |

TABLE 2-continued

Stress-strain measurements of monomeric compositions of PHN and PHO

| Sample | Annealing time at room temp. (h) | Thickness (mm) | Tensile stress at maximum load (MPa) | Young's modulus (MPa) | Elongation at break (%) |
|---|---|---|---|---|---|
| PHO-88 | 66 | 1.28 ± 0.01 | 9.0 ± 1.0 | 3.3 ± 0.1 | 1300 ± 100 |
| PHO-94 | 66 | 1.34 ± 0.01 | 11.7 ± 0.5 | 4.7 ± 0.2 | 1270 ± 100 |

We claim:

1. A method of making MCL-PHA polymer, comprising:
providing MCL-PHA-producing microbial cells in a medium suitable for microbial growth, the medium comprising:
a substrate that is structurally related to MCL-PHA;
a carbon source that is not structurally related to MCL-PHA; and
a β-oxidation pathway inhibitor; and
allowing microbial cell growth to occur in the medium wherein the microbial cells synthesize MCL-PHA polymer;
wherein the MCL-PHA polymer is a homopolymer or a copolymer that has a selected ratio of comonomers that differs from that obtained in the absence of the β-oxidation pathway inhibitor;
wherein microbial cell growth and MCL-PHA copolymer production take place in a carbon-limited fed-batch or a carbon-limited continuous fermentation process.

2. The method of claim 1, wherein the carbon source is added in a fed-batch manner or a continuous manner.

3. The method of claim 1, wherein the substrate and the carbon source are co-fed during fermentation.

4. The method of claim 1, wherein the molar ratio of substrate:carbon source is selected such that there is substantially no production of unwanted monomers or such that there is substantially no toxic accumulation of the substrate structurally related to MCL-PHA.

5. The method of claim 1, wherein the molar ratio of substrate:carbon source is selected such that microbial cell growth is not inhibited.

6. The method of claim 1, wherein the molar ratio of substrate:carbon source is 1 or higher when glucose is the carbon source.

7. The method of claim 6, wherein the molar ratio of substrate:carbon source is about 1.1 to about 1.2 when glucose is the carbon source.

8. The method of claim 6, wherein the molar ratio of substrate:carbon source is about 1.4 to about 1.5 when glucose is the carbon source.

9. The method of claim 1, wherein the molar ratio of substrate:carbon source is between about 1 and about 1.5 when glucose is the carbon source.

10. The method of claim 1, wherein the concentration of biomass generated is about 25 g/L or more, about 40 g/L or more, or about 60 g/L or more.

11. The method of claim 1, wherein the structurally-related substrate is a $C_6$-$C_{18}$ fatty acid.

12. The method of claim 11, wherein the structurally-related substrate is hexanoic acid, heptanoic acid, octanoic acid, nonanoic acid, decanoic acid, undecanoic acid, or dodecanoic acid.

13. The method of claim 1, wherein the carbon source is not susceptible to β-oxidation.

14. The method of claim 1, wherein the MCL-PHA-producing microbial cells are of the genus *Pseudomonas*.

15. The method of claim 1, wherein the structurally-related substrate is a functionalized fatty acid.

16. The method of claim 15, wherein the functionalized fatty acid is a functionalized hexanoic acid, functionalized heptanoic acid, functionalized octanoic acid, functionalized nonanoic acid, functionalized decanoic acid, functionalized undecanoic acid, or functionalized dodecanoic acid.

17. The method of claim 1, wherein the β-oxidation pathway inhibitor is acrylic acid, 2-butynoic acid, 2-octynoic acid, phenylpropionic acid, propionic acid, trans-cinnamic acid, salicylic acid, methacrylic acid, 4-pentenoic acid, or 3-mercaptopropionic acid.

18. The method of claim 1, wherein the carbon source is a carbohydrate, glycerol, citric acid, acetic acid, lactic acid, or a combination thereof.

19. The method of claim 18, wherein the carbon source is glucose or sucrose.

20. The method of claim 1, further comprising collecting and purifying the MCL-PHA.

21. A polyhydroxyalkanoate polymer produced by the method of claim 1, that is at least about 89 mol % or higher of a selected monomer.

22. The polyhydroxyalkanoate polymer of claim 21, wherein the at least about 89 mol % is 89 mol %, 90 mol %, 95 mol % or 99 mol.

23. The polyhydroxyalkanoate polymer of claim 21, wherein the structurally-related substrate is hexanoic acid, heptanoic acid, octanoic acid, nonanoic acid; decanoic acid, undecanoic acid, or dodecanoic acid.

24. The polyhydroxyalkanoate polymer of claim 21, wherein the β-oxidation pathway inhibitor is acrylic acid, 2-butynoic acid, 2-octynoic acid, phenylpropionic acid, propionic acid, trans-cinnamic acid, salicylic acid, methacrylic acid, 4-pentenoic acid, or 3-mercaptopropionic acid.

25. Polyhydroxyalkanoate polymer comprising a $C_n$ monomer that has n carbons, wherein n is 6, 7, 8, 9, or 11 to 18, and
wherein when n is 6, 7, 9, or 11, the polymer is at least about 85 mol % or higher $C_n$ monomer,
wherein when n is 8, the polymer is at least about 97 mol % or higher $C_n$ monomer, and
wherein when n is 12 to 18, the polymer is at least about 70 mol % or higher $C_n$ monomer.

26. The polyhydroxyalkanoate polymer (PHN) of claim 25 wherein n is 9, comprising about 85 mol % or higher 3-OH-nonanoate.

27. The PHN of claim 26, comprising about 86, about 88, about 90, about 92, about 94, about 95, or about 96 mol % 3-OH-nonanoate.

28. The polyhydroxyalkanoate polymer (PHN) of claim 25 wherein n is 8, comprising about 97 mol % or higher 3-OH-octanoate.

29. The PHN of claim 28, comprising about 97, or about 98 mol % 3-OH-octanoate.

30. The polyhydroxyalkanoate polymer (PHN) of claim 25 wherein n is 12, comprising about 70 mol % or higher 3-OH-dodecanoate.

31. The PHN of claim 30, comprising at least about 80 mol % or higher 3-OH-dodecanoate.

32. The polyhydroxyalkanoate polymer (PHN) of claim 25 wherein n is 12, comprising at least about 60 mol % or higher 3-OH-dodecanoate.

33. The method of claim 1, wherein the MCL-PHA-producing microbial cells are genetically modified microorganisms.

34. The method of claim 33, wherein the genetic modification:
increases production of PHA, increases oxygen uptake capacity, increases solvent toxicity resistance, decreases autolysis, modifies the ratio of PHA comonomers, or any combination thereof.

35. The method of claim 34, wherein modifying the ratio of PHA comonomers is increasing the amount of predominant monomer.

36. The method of claim 1, wherein the MCL-PHA-producing microbial cells are naturally occurring.

37. The polyhydroxyalkanoate polymer of claim 28, further comprising a $C_{n-2}$ monomer that has n−2 carbons.

38. A method of making MCL-PHA polymer, comprising:
providing MCL-PHA-producing microbial cells in a medium suitable for microbial growth, the medium comprising:
a substrate that is structurally related to MCL-PHA;
a carbon source that is not structurally related to MCL-PHA; and
a β-oxidation pathway inhibitor; and
allowing microbial cell growth to occur in the medium wherein the microbial cells synthesize MCL-PHA polymer;
wherein the MCL-PHA polymer is a homopolymer or a copolymer that has a selected ratio of comonomers that differs from that obtained in the absence of the β-oxidation pathway inhibitor;
wherein the molar ratio of substrate:carbon source is between about 1 and about 1.5 when glucose is the carbon source.

* * * * *

UNITED STATES PATENT AND TRADEMARK OFFICE
CERTIFICATE OF CORRECTION

PATENT NO.        : 8,273,852 B2
APPLICATION NO.   : 12/960156
DATED             : September 25, 2012
INVENTOR(S)       : Xuan Jiang et al.

It is certified that error appears in the above-identified patent and that said Letters Patent is hereby corrected as shown below:

In the Claims:

Column 30, Line 1, Claim 37
"28" should be --25--

Column 30, Line 2, Claim 37
"$C_n$-2" should be --$C_{n-2}$--

Signed and Sealed this
Twentieth Day of November, 2012

David J. Kappos
*Director of the United States Patent and Trademark Office*